United States Patent

Kehne et al.

[11] Patent Number: 5,849,666
[45] Date of Patent: Dec. 15, 1998

[54] N-SUBSTITUTED HYDRAZINOPHENYLSULFONYLUREAS, PROCESSES FOR THEIR PREPARATION AND THEIR USE AS HERBICIDES AND PLANT GROWTH REGULATIONS

[75] Inventors: Heinz Kehne; Lothar Willms, both of Hofheim; Klaus Bauer, Hanau; Hermann Bieringer, Eppstein; Christopher Rosinger, Hofheim, all of Germany

[73] Assignee: Hoechst Schering Agrevo GmbH, Berlin, Germany

[21] Appl. No.: 562,043

[22] Filed: Nov. 22, 1995

[30] Foreign Application Priority Data

Nov. 28, 1994 [DE] Germany .......................... 44 42 236.9

[51] Int. Cl.$^6$ ..................... C07D 239/64; C07D 401/12; C07D 403/12; A01N 43/54

[52] U.S. Cl. .................. 504/214; 504/215; 544/321; 544/323; 544/324; 544/332; 544/238; 544/120; 544/121; 544/122; 544/123; 544/295; 544/296

[58] Field of Search ............................ 504/214, 215; 544/321, 323, 324, 332, 238, 120, 121, 122, 123, 295, 296

[56] References Cited

U.S. PATENT DOCUMENTS

| | | | |
|---|---|---|---|
| 5,591,694 | 1/1997 | Hamprecht | 504/214 |
| 5,612,286 | 3/1997 | Mayer et al. | 504/214 |
| 5,648,315 | 7/1997 | Lorenz et al. | 504/214 |
| 5,658,854 | 8/1997 | Schnabel et al. | 504/214 |
| 5,723,409 | 3/1998 | Schnabel et al. | 504/214 |

FOREIGN PATENT DOCUMENTS

| | | |
|---|---|---|
| 0 382 436 | 8/1990 | European Pat. Off. . |
| 0 382 437 | 8/1990 | European Pat. Off. . |
| 0 384 602 | 8/1990 | European Pat. Off. . |
| 0 562 575 | 9/1993 | European Pat. Off. . |

OTHER PUBLICATIONS

Cram and Hammond Organic Chemistry, 2nd Edition, pp. 565–567, McGraw Hill Book Co., New York, 1964.

*Primary Examiner*—John M. Ford
*Attorney, Agent, or Firm*—Frommer Lawrence & Haug LLP

[57] ABSTRACT

N-substituted hydrazinophenylsulfonylureas, processes for their preparation and their use as herbicides and plant growth regulators Compounds of the formula (I) or salts thereof

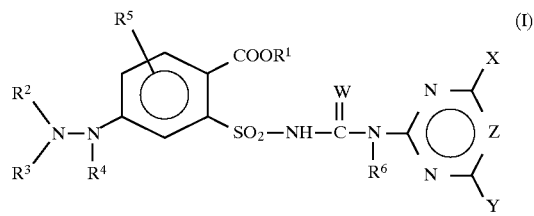

in which $R^1$ to $R^6$, W, Q, X, Y and Z are defined as in formula (I) as claimed in claim 1, are suitable as herbicides and plant growth regulators.

The compounds (I) are prepared by processes analogous to known processes (cf. claim 5), in some cases via novel intermediates of the formula (II)

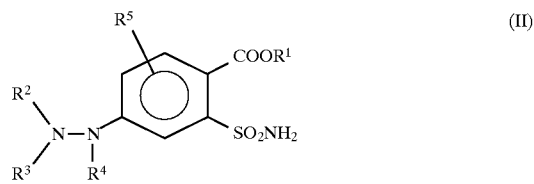

5 Claims, No Drawings

N-SUBSTITUTED HYDRAZINOPHENYLSULFONYLUREAS, PROCESSES FOR THEIR PREPARATION AND THEIR USE AS HERBICIDES AND PLANT GROWTH REGULATIONS

DESCRIPTION

N-substituted hydrazinophenylsulfonylureas, processes for their preparation and their use as herbicides and plant growth regulators It is known that phenylsulfonylureas with hydrazine partial structures have herbicidal properties. These are chiefly hydrazones (EP-A-382 437, EP-A-562 575) or heterocyclic compounds with an incorporated hydrazine structure (EP-A-382 436, EP-A-384 602).

Surprisingly, phenylsulfonylureas with substituted hydrazine radicals have now been found which are particularly suitable as herbicides or plant growth regulators.

The present invention relates to compounds of the formula (I) or salts thereof

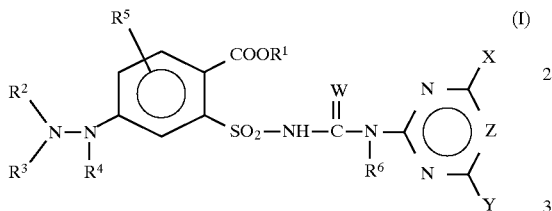

in which
- $R^1$ is a hydrogen atom, a hydrocarbon radical or a heterocyclyl radical, where each of the last two radicals mentioned is unsubstituted or substituted and, including substituents, has preferably 1 to 20 carbon atoms,
- $R^2$, $R^3$ and $R^4$ independently of one another are a radical of the formula $A^1$ or $A^2$, where at least one of the radicals $R^2$, $R^3$ and $R^4$ has the meaning of $A^1$,
- $R^5$ is H, halogen, $NO_2$, CN, $(C_1-C_4)$alkyl, $(C_1-C_4)$alkoxy, $[(C_1-C_4)$alkyl$]$carbonyl or $[(C_1-C_4)$alkoxy$]$carbonyl, where each of the last four radicals mentioned is unsubstituted or substituted in the alkyl part by one or more halogen atoms,
- $R^6$ is H or $(C_1-C_4)$alkyl, preferably H or $CH_3$,
- $A^1$ is a substituted aliphatic hydrocarbon radical having 1 to 6 carbon atoms in the hydrocarbon part and one or more substituents, where the substituents are chosen from the group consisting of halogen, $(C_1-C_4)$alkoxy, $(C_1-C_4)$alkylthio, $(C_1-C_4)$alkylsulfonyl, $[(C_1-C_4)$alkyl$]$carbonyl, $[(C_1-C_4)$alkoxy$]$carbonyl, CN, substituted or unsubstituted phenyl and $(C_3-C_6)$cycloalkyl, or $(C_2-C_6)$alkenyl or $(C_2-C_6)$alkynyl, or an acyl radical having preferably 1 to 20 carbon atoms,
- $A^2$ is a radical analogous to $A^1$ or hydrogen or $(C_1-C_6)$alkyl,
- Q is O or NR*,
- R* is H, $(C_1-C_4)$alkyl, $(C_3-C_4)$alkenyl or $(C_3-C_4)$alkynyl, where each of the last three radicals mentioned is unsubstituted or substituted by one or more radicals from the group consisting of halogen, $(C_1-C_4)$alkoxy and $(C_1-C_4)$alkylthio,
- W is an oxygen or sulfur atom,
- X and Y independently of one another are H, halogen, $(C_1-C_4)$alkyl, $(C_1-C_4)$alkoxy or $(C_1-C_4)$alkylthio, where each of the last 3 radicals mentioned is unsubstituted or substituted by one or more radicals from the group consisting of halogen, $(C_1-C_4)$alkoxy and $(C_1-C_4)$alkylthio, or mono- or di-$[(C_1-C_4)$alkyl$]$amino, $(C_3-C_6)$cycloalkyl, $(C_2-C_5)$alkenyl, $(C_2-C_5)$alkynyl, $(C_2-C_5)$alkenyloxy or $(C_2-C_5)$alkynyloxy and
- Z is CH or N.

The compounds of the formula (I) can form salts in which the hydrogen of the —$SO_2$—NH-group is replaced by a cation suitable for agriculture. These salts are, for example, metal salts, in particular alkali metal salts or alkaline earth metal salts, in particular sodium and potassium salts, or also ammonium salts or salts with organic amines. Salt formation can likewise occur by addition of an acid onto basic groups, such as, for example, amino and alkylamino. Suitable acids for this are strong inorganic and organic acids, for example HCl, HBr, $H_2SO_4$ or $HNO_3$.

In formula (I) and all the following formulae, the alkyl, alkoxy, haloalkyl, haloalkoxy, alkylamino and alkylthio radicals and the corresponding unsaturated and/or substituted radicals can in each case be straight-chain or branched in the carbon skeleton. Unless specifically stated, the lower carbon skeletons, for example having 1 to 6 carbon atoms, or in the case of unsaturated groups having 2 to 6 carbon atoms, are preferred for these radicals. Alkyl radicals, including those in the composite meanings, such as alkoxy, haloalkyl and the like, are, for example, methyl, ethyl, n- or i-propyl, n-, i-, t- or 2-butyl, pentyl radicals, hexyl radicals, such as n-hexyl, i-hexyl and 1,3-dimethylbutyl, or heptyl radicals, such as n-heptyl, 1-methylhexyl and 1,4-dimethylpentyl; alkenyl and alkynyl radicals have the meaning of the possible unsaturated radicals corresponding to the alkyl radicals; alkenyl is, for example, allyl, 1-methyl-prop-2-en-1-yl, 2-methyl-prop-2-en-1-yl, but-2-en-1-yl, but-3-en-1-yl, 1-methyl-but-3-en-1-yl and 1-methyl-but-2-en-1-yl; and alkynyl is, for example, propargyl, but-2-yn-1-yl, but-3-yn-1-yl and 1-methyl-but-3-yn-1-yl. Alkenyl in the form "$(C_3-C_4)$alkenyl" or "$(C_3-C_6)$alkenyl" is preferably an alkenyl radical having 3 to 4 or 3 to 6 carbon atoms, in which the double bond is not between C-1 and C-2 (C-1 is the position with "yl").

Cycloalkyl is a carbocyclic saturated ring system having preferably 3–8 carbon atoms, for example cyclopropyl, cyclopentyl or cyclohexyl.

Halogen is, for example, fluorine, chlorine, bromine or iodine. Haloalkyl, -alkenyl and -alkynyl are alkyl, alkenyl or alkynyl, respectively, which are partly or completely substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$ and $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the corresponding definition applies to haloalkenyl and other radicals substituted by halogen.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl; aryl here is a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms or phenyl; the corresponding definition applies to a hydrocarbon radical in a hydrocarbonoxy radical.

A heterocyclic radical or ring (heterocyclyl) can be saturated, unsaturated or heteroaromatic; it preferably contains one or more hetero units in the ring, preferably from the group consisting of N, O, S, SO and $SO_2$; preferably, it is an aliphatic heterocyclyl radical having 3 to 7 ring atoms or a heteroaromatic radical having 5 or 6 ring atoms and contains 1, 2 or 3 hetero units. The heterocyclic radical can be, for example, a heteroaromatic radical or ring (heteroaryl), such as, for example, a mono-, bi- or polycyclic aromatic system in which at least 1 ring contains one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or is a partly or completely hydrogenated radical, such as oxiranyl, pyrrolidyl, piperidyl, piperazinyl, dioxolanyl, morpholinyl or tetrahydrofuryl. Possible substituents for a substituted heterocyclic radical are the substituents mentioned below, and in addition also oxo. The oxo group can also occur on the hetero ring atoms which can exist in different oxidation levels, for example in the case of N and S. Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical derived from the unsubstituted parent substance, the substituents being, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino and mono- and dialkylamino, and alkylsulfinyl, haloalkylsulfinyl, alkylsulfonyl, haloalkylsulfonyl and, in the case of cyclic radicals, also alkyl and haloalkyl, as well as unsaturated aliphatic radicals corresponding to the saturated hydrocarbon-containing radicals mentioned, such as alkenyl, alkynyl, alkenyloxy, alkynyloxy and the like. In the case of radicals with carbon atoms, those having 1 to 4 carbon atoms, in particular 1 or 2 carbon atoms, are preferred. Substituents from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano, are as a rule preferred. The substituents methyl, methoxy and chlorine are particularly preferred here.

Mono- or disubstituted amino is a chemically stable radical from the group consisting of substituted amino radicals which are N-substituted, for example by one or two identical or different radicals from the group consisting of alkyl, alkoxy, acyl and aryl; preferably monoalkylamino, dialkylamino, acylamino, arylamino, N-alkyl-N-arylamino and N-heterocyclic radicals; alkyl radicals having 1 to 4 carbon atoms are preferred here; aryl here is preferably phenyl or substituted phenyl; the definition given below applies here to acyl, preferably $(C_1-C_4)$alkanoyl. A corresponding definition applies to substituted hydroxylamino or hydrazino.

Optionally substituted phenyl is preferably phenyl which is unsubstituted or mono- or polysubstituted, preferably up to three times, by identical or different radicals from the group consisting of halogen, $(C_1-C_4)$alkyl, $(C_1-C_4)$alkoxy, $(C_1-C_4)$halogenalkyl, $(C_1-C_4)$halogenalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl and o-, m- and p-methoxyphenyl.

An acyl radical is the radical of an organic acid, for example the radical of a carboxylic acid and radicals of acids derived therefrom, such as of thiocarboxylic acid, optionally N-substituted iminocarboxylic acids or the radical of carbonic acid monoesters, optionally N-substituted carbamic acid, sulfonic acids, sulfinic acids, phosphonic acids and phosphinic acids. Acyl is, for example, formyl, alkylcarbonyl, such as $(C_1-C_4\text{-alkyl})$carbonyl, phenylcarbonyl, in which the phenyl ring can be substituted, for example as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The invention also relates to all the stereoisomers included by the formula (I) and mixtures thereof. Such compounds of the formula (I) contain one or more asymmetric carbon atoms or double bonds which are not shown separately in the formula (I). The possible stereoisomers defined by their specific spatial form, such as enantiomers, diastereomers and Z and E isomers, are all included by the formula (I) and can be obtained from mixtures of the stereoisomers by customary methods or else prepared by stereoselective reactions in combination with the use of stereochemically pure starting substances.

The above examples of radicals or radical ranges falling under general terms such as "alkyl", "acyl", "substituted radicals" and the like are not a complete list. The general terms also include the definitions given below for ranges of radicals in groups of preferred compounds, in particular ranges of radicals which include specific radicals from the tabular examples.

Compounds of the formula (I) or salts thereof which are of particular interest, above all for reasons of a higher herbicidal action, better selectivity and/or easier preparation, are those in which $R^1$ is H, $(C_1-C_6)$alkyl, $(C_3-C_6)$alkenyl or $(C_3-C_6)$alkynyl, where each of the last three radicals mentioned is unsubstituted or substituted by one or more radicals from the group consisting of halogen, phenyl, $(C_1-C_4)$alkoxy, $(C_1-C_4)$alkylthio and $[(C_1-C_4)$alkoxy]carbonyl, or $(C_3-C_6)$cycloalkyl, $(C_3-C_6)$cycloalkyl $(C_1-C_3)$alkyl, heterocyclyl having 3 to 6 ring atoms or heterocyclyl-$(C_1-C_3)$alkyl having 3 to 6 ring atoms, where each of the last 4 radicals mentioned is unsubstituted or substituted by one or more radicals from the group consisting of halogen, $(C_1-C_4)$alkyl and $(C_1-C_4)$alkoxy, $A^1$ is $(C_1-C_6)$alkyl, which is substituted by one or more radicals from the group consisting of halogen, $(C_1-C_4)$alkoxy, $(C_1-C_4)$alkylthio, $(C_1-C_4)$alkylsulfonyl, $[(C_1-C_4)$alkoxy]carbonyl, CN, phenyl and $(C_3-C_6)$cycloalkyl, or $(C_3-C_6)$alkenyl or $(C_3-C_6)$alkynyl, where each of the last two radicals mentioned is unsubstituted or substituted by one or more halogen atoms, of a group of the formula

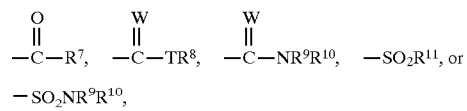

$A^2$ is a radical analogous to $A^1$ or hydrogen or $(C_1-C_4)$alkyl, $R^7$ is H, $(C_1-C_8)$alkyl, $(C_2-C_6)$alkenyl or $(C_2-C_6)$alkynyl, where each of the last three radicals mentioned is unsubstituted or substituted by one or more radicals from the group consisting of halogen, $(C_1-C_4)$alkoxy, $(C_1-C_4)$alkylthio, phenoxy, $[(C_1-C_4)$alkoxy]carbonyl, unsubstituted or substituted heterocyclyl and unsubstituted or substituted phenyl, or unsubstituted or substituted $(C_3-C_6)$cycloalkyl, unsubstituted or substituted phenyl, unsubstituted or substituted heterocyclyl or $[(C_1-C_4)$alkoxy]carbonyl, $R^8$ is a radical analogous to $R^7$, apart from hydrogen, preferably $(C_1-C_6)$alkyl, $(C_3-C_6)$alkenyl or $(C_3-C_6)$alkynyl, where each of the last three radicals mentioned is unsubstituted or substituted by one or more radicals from the group consisting of halogen, $(C_1-C_4)$alkoxy, $(C_1-C_4)$alkylthio, $[(C_1-C_4)$-alkoxy]carbonyl, unsubstituted or substituted phenyl and unsubstituted or substituted $(C_3-C_6)$cycloalkyl, or $(C_3-C_6)$cycloalkyl, which is unsubstituted or substituted by one or more radicals from the group consisting of halogen, $(C_1-C_4)$alkyl and $(C_1-C_4)$alkoxy, $R^9$ and $R^{10}$ independently of one another are H, $(C_1-C_6)$alkyl, $(C_3-C_6)$alkenyl or $(C_3-C_6)$alkynyl, where each of the last three radicals mentioned is unsubstituted or substituted by one or more radicals from the group consisting of halogen, $(C_1-C_4)$alkoxy, $(C_1-C_4)$alkylthio and $[(C_1-C_4)$alkyl]carbonyl, or unsubstituted or substituted phenyl, or $R^9$ and $R^{10}$, together with the N atom, are a heterocyclic ring having 5 or 6 ring members, which can optionally contain further hetero atoms from the group consisting of N, O and S and is unsubstituted or mono- or polysubstituted by $(C_1-C_4)$alkyl or an oxo group, $R^{11}$ is $(C_1-C_6)$alkyl, $(C_3-C_6)$alkenyl or $(C_3-C_6)$alkynyl, where each of the last three radicals mentioned is unsubstituted or substituted by one or more radicals from the group consisting of halogen, $(C_1-C_4)$alkoxy, $(C_1-C_4)$alkylthio and phenyl, or phenyl, which is unsubstituted or substituted by one or more radicals from the group consisting of halogen, CN, $NO_2$ $(C_1-C_4)$alkyl, $(C_1-C_4)$haloalkyl and $(C_1-C_4)$alkoxy, Q is O or NR*, R* is defined as above, W is O or S, T is O or S, X and Y independently of one another are H, halogen, $(C_1-C_4)$alkyl, $(C_1-C_4)$alkoxy or $(C_1-C_4)$alkylthio, where each of the last three radicals mentioned is unsubstituted or substituted by one or more radicals from the group consisting of halogen, $(C_1-C_3)$alkoxy and $(C_1-C_4)$alkylthio, or mono- or di$[(C_1-C_4)$alkyl]amino, $(C_3-C_6)$-cycloalkyl, $(C_3-C_5)$alkenyl, $(C_3-C_5)$alkenyloxy or $(C_3-C_5)$alkynyloxy and/or Z is CH or N.

Compounds of the formula (I) according to the invention and salts thereof which are also of particular interest are those in which $R^1$ is $(C_1-C_6)$alkyl, which is unsubstituted or substituted by one or more radicals from the group consisting of halogen and $(C_1-C_4)$alkoxy, or $(C_3-C_4)$alkenyl or $(C_3-C_4)$alkynyl, or heterocyclyl having 3 to 6 ring atoms and 1 or 2 hetero ring atoms from the group consisting of N and O, for example 3-oxetanyl, $R^2$ is a group of the formula

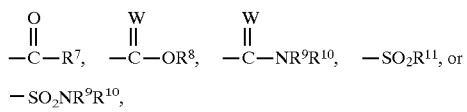

$R^3$ is H, $(C_1-C_4)$alkyl, which is unsubstituted or substituted by one or more radicals from the group consisting of halogen, $(C_1-C_4)$alkoxy, $(C_1-C_4)$alkylthio, $[(C_1-C_4)$-alkoxy]carbonyl and phenyl, or $(C_3-C_4)$alkenyl or $(C_3-C_4)$alkynyl, or $R^4$ is H, $(C_1-C_4)$alkyl, which is unsubstituted or substituted by one or more radicals from the group consisting of halogen, $(C_1-C_4)$alkoxy, $(C_1-C_4)$alkylthio, $[(C_1-C_4)$alkoxy]carbonyl and phenyl, or $(C_3-C_4)$alkenyl or $(C_3-C_4)$alkynyl, $R^5$ is H, $(C_1-C_4)$alkyl, $(C_1-C_4)$haloalkyl, $(C_1-C_4)$alkoxy or halogen, $R^6$ is H or methyl, $R^7$ is H, $(C_1-C_6)$alkyl, which is unsubstituted or substituted by one or more radicals from the group consisting of halogen, $(C_1-C_4)$alkoxy, $(C_1-C_4)$ alkylthio, $[(C_1-C_4)$alkoxy]carbonyl and unsubstituted or substituted phenyl, or $(C_2-C_4)$alkenyl, $(C_2-C_4)$alkynyl, $(C_3-C_6)$cycloalkyl, $[(C_1-C_4)$alkoxy]carbonyl, unsubstituted or substituted phenyl or unsubstituted or substituted heterocyclyl, $R^8$ is $(C_1-C_4)$alkyl, $(C_1-C_4)$haloalkyl, $(C_3-C_4)$alkenyl, $(C_3-C_4)$alkynyl or $(C_3-C_6)$cycloalkyl, $R^9$ and $R^{10}$ independently of one another are H, $(C_1-C_4)$alkyl, which is unsubstituted or substituted by one or more radicals from the group consisting of halogen and $(C_1-C_4)$alkoxy, or $(C_3-C_4)$alkenyl or $(C_3-C_4)$alkynyl, or $R^9$ and $R^{10}$, together with the N atom, are a heterocyclic ring having 5 or 6 ring members, which can optionally contain a further hetero atom from the group consisting of N, O and S and is unsubstituted or mono- or polysubstituted by $(C_1-C_4)$alkyl or an oxo group, $R^{11}$ is $(C_1-C_6)$alkyl, $(C_1-C_4)$haloalkyl or phenyl, which is unsubstituted or substituted by one or more radicals from the group consisting of halogen, $(C_1-C_4)$alkyl and $(C_1-C_4)$alkoxy, R* is H or $(C_1-C_4)$alkyl, X and Y independently of one another are $(C_1-C_4)$alkyl or $(C_1-C_4)$alkoxy, where each of the last two radicals mentioned is unsubstituted or substituted by one or more halogen atoms, or $(C_1-C_4)$alkylthio, halogen or mono- or di$[(C_1-C_2)$alkyl]amino and/or W is an oxygen atom.

Preferred compounds of the formula (I) or salts thereof are those in which $R^2$ is the formulae

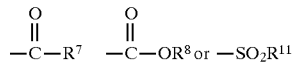

and $R^3$ and $R^4$ independently of one another are H, $(C_1-C_4)$alkyl, $(C_3-C_4)$alkenyl or $(C_3-C_4)$alkynyl, $R^5$ is H, $(C_1-C_4)$alkyl or halogen, $R^7$ is H, $(C_1-C_4)$alkyl, which is unsubstituted or substituted by one or more radicals from the group consisting of halogen, $(C_1-C_4)$alkoxy and phenyl, or $(C_2-C_4)$ alkenyl, $(C_3-C_6)$cycloalkyl or phenyl, which is unsubstituted or substituted by one or more radicals from the group consisting of halogen, $(C_1-C_4)$alkyl and $(C_1-C_3)$ alkoxy, $R^8$ is $(C_1-C_4)$alkyl or $(C_1-C_4)$haloalkyl, $R^{11}$ is $(C_1-C_3)$alkyl or $(C_1-C_3)$haloalkyl, R* is $(C_1-C_3)$alkyl, X is $(C_1-C_2)$alkyl, $(C_1-C_2)$alkoxy, $(C_1-C_2)$alkylthio, $(C_1-C_2)$haloalkyl or $(C_1-C_2)$haloalkoxy and Y is $(C_1-C_2)$alkyl, $(C_1-C_2)$alkoxy, halogen, $NHCH_3$ or $N(CH_3)_2$.

Particularly preferred compounds of the formula (I) or salts thereof are those in which $R^1$ is methyl, ethyl, allyl or propargyl, $R^2$ is a radical of the formula $A^1$ as is defined above, in particular the meanings mentioned as preferred for this, $R^3$ and $R^4$ are each H, $R^5$ is H and Q is an oxygen atom.

The present invention also relates to processes for the preparation of the compounds of the formula (I) or salts thereof, which comprises a) reacting a compound of the formula (II)

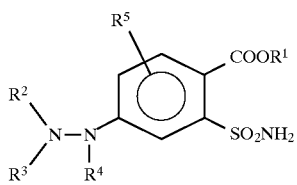
(II)

with a heterocyclic carbamate of the formula (III)

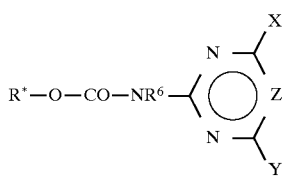
(III)

in which R* is unsubstituted or substituted phenyl or $(C_1-C_4)$alkyl, or b) reacting a sulfonylcarbamate of the formula (IV)

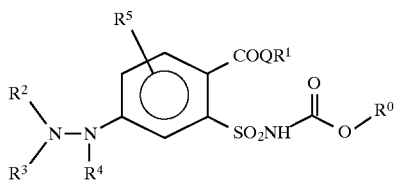
(IV)

in which $R^0$ is unsubstituted or substituted phenyl or $(C_1-C_4)$alkyl, with an amino-heterocyclic compound of the formula (V)

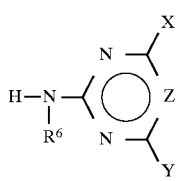
(V)

or c) reacting a sulfonyl isocyanate of the formula (VI)

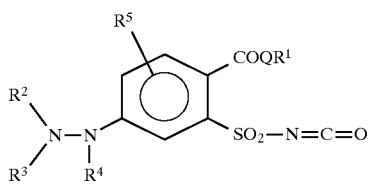
(VI)

with an amino-heterocyclic compound of the formula (V), or d) reacting a sulfonamide of the formula (II) with a (thio)isocyanate of the formula (VII)

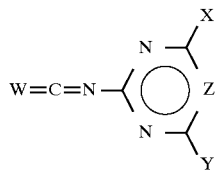
(VII)

in the presence of a base, or e) first reacting an amino-heterocyclic compound of the formula (V) with a carbonic acid ester, for example diphenyl carbonate, under base catalysis and reacting the intermediate formed with a sulfonamide of the formula (II) in a one-pot reaction, in which, in the formulae (II)–(VII), the radicals and groups $R^1$–$R^6$, Q, W, X, Y and Z are defined as in formula (I) and in process variants a) to c) and e) compounds of the formula (I) where W=O are initially obtained.

The reaction of the compounds of the formulae (II) and (III) is preferably carried out under base catalysis in an inert organic solvent, such as, for example, methylene chloride, acetonitrile, dioxane or tetrahydrofuran, at temperatures between 0° C., preferably 20° C., and the boiling point of the solvent. Bases which are used here are, for example, organic amine bases, such as 1,8-diazabicyclo[5.4.0]undec-7-ene (DBU), especially if $R^0$=(substituted) phenyl (cf. EP-A-44807), or trimethylaluminum or triethylaluminum, the latter especially if $R^0$=alkyl (cf. EP-A-166 516). The particular base is employed here, for example, in the range from 1 to 3 molar equivalents, based on the compound of the formula (II).

The sulfonamides (II) are novel compounds. This invention likewise relates to them and their preparation.

The compounds of the formula (II) are obtained, for example, starting from compounds of the formula (VIII)

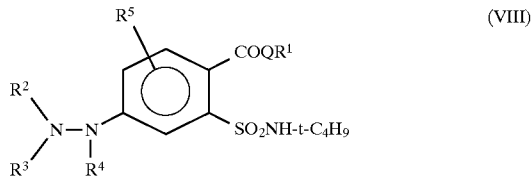
(VIII)

in which $R^1$–$R^5$ are defined as in formula (I), by reaction with a strong acid (in this context, cf. WO 89/10921).

Possible strong acids are, for example, mineral acids, such as $H_2SO_4$ or HCl, or strong organic acids, such as trifluoroacetic acid. The tert-butyl protective group is split off, for example, at temperatures between −20° C. and the particular reflux temperature of the reaction mixture, preferably at 0° C. to 40° C. The reaction can be carried out in bulk or also in an inert solvent, such as, for example, methylene chloride or chloroform.

The compounds of the formula (VIII) are obtained, for example, from suitable hydrazine precursors by reaction with suitable electrophiles, such as, for example, acid chlorides, acid anhydrides, isocyanates, isothiocyanates, sulfochlorides or sulfamoyl chlorides. Suitable hydrazine precursors are, for example, those in which $R^2$=H and $R^3$ and $R^4$ are defined as in formula (I), $R^2$ and $R^4$=H and R is defined as in formula (I), $R^2$ and $R^3$=H and $R^4$ is defined as in formula (I), but in particular $R^2$, $R^3$ and $R^4$=H. (For reaction of the hydrazine precursors with electrophiles cf.:

K. H. Pilgram, Synth. Commun. 15, 697 (1985),

J. Knabe, W. Wunn, Arch. Pharm. 313, 577 (1980)

V. Lerch, J. König, Synthesis, 157 (1983),

R. F. Smith et al., J. Org. Chem. 33, 851 (1968),
K. H. Pilgram, J. Org. Chem. 53, 38 (1988),
U.S. Pat. No. 4,619,689, EP-A-562 575,
Houben-Weyl, "Methoden der organischen Chemie" (Methods of organic chemistry), 4th edition, volume 10/2, p. 355 et seq, p. 383 et seq, p. 396 et seq, p. 406 et seq, p. 391 et seq).

In some cases, it is possible to carry out further derivatizations by methods known from the literature after the reaction with electrophiles, for example alkylations or acylations (cf. Houben-Weyl, "Methoden der organischen Chemie" (Methods of organic chemistry), 4th edition, volume 10/2, p. 402 et seq and p. 385).

The phenylhydrazines of the formula (VIII) where $R^2$, $R^3$ and $R^4$=H are accessible starting from the aniline derivatives (IX)

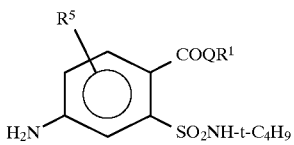

in which $R^1$ and $R^5$ are defined as in formula (I), by diazotization and subsequent reduction. Suitable reducing agents are, for example, $SnCl_2$, $SO_2$ or sodium dithionite (cf. Houben-Weyl, "Methoden der organischen Chemie" (Methods of organic chemistry), 4th edition, volume 10/2, p. 180 et seq; EP-A-562 575).

The aniline derivatives of the formula (IX) mentioned are obtained by processes known from the literature by reduction of the nitro group of the compounds (X), for example by hydrogenation with hydrogen in the presence of a suitable catalyst, such as Pd-C or Raney nickel, or by reduction with iron in an acetic acid medium.

(In this context, cf.: H. Berrie, G. T. Neuhold, F. S. Spring, J. Chem. Soc. (1952), 2042; M. Freifelder, "Catalytic Hydrogenation in Organic Synthesis: Procedures and Commentary", J. Wiley and Sons, New York (1978), chapter 5.)

The aromatic sulfonamides of the formula (X) can be obtained from the sulfonic acids of the formula (XI)

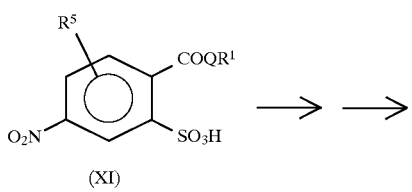

The sulfonic acid group of the compounds (XI) is first converted into the sulfochlorides, for example by standard methods, such as reaction of phosphorus oxychloride or thionyl chloride with potassium salts of the corresponding sulfonic acids in inert solvents, such as acetonitrile and/or sulfolane, or in bulk by heating under reflux (cf. Houben-Weyl-Klamann, "Methoden der organischen Chemie" (Methods of organic chemistry), 4th edition, volume E X1/2, p. 1067–1073, Thieme Verlag Stuttgart, 1985).

The formation of sulfonamides from the sulfochlorides with tert-butylamine in ethanol or THF gives the compounds (X) in good yields (cf. analogous reactions in WO 89/10921).

The sulfonic acids of the formula (XI) can be prepared from commercially obtainable 2-methyl-5-nitrobenzenesulfonic acid.

The substituent $COOR^1$ is introduced by oxidation of the methyl group of 2-methyl-5-nitrobenzenesulfonic acid by standard methods, such as, for example, reaction with potassium permanganate to give the carboxylic acid function and subsequent esterification. (In this context, cf.: Houben-Weyl-Falbe: "Methoden der organischen Chemie" (Methods of organic chemistry), 4th edition, volume E V/1, Thieme Verlag Stuttgart, 1985, p. 199–202).

As an alternative to this, the intermediate products of the formula (Xa) (carboxylic acid derivatives) are also accessible starting from commercially available 2-amino-5-nitrobenzoic acid in accordance with the following reaction equation

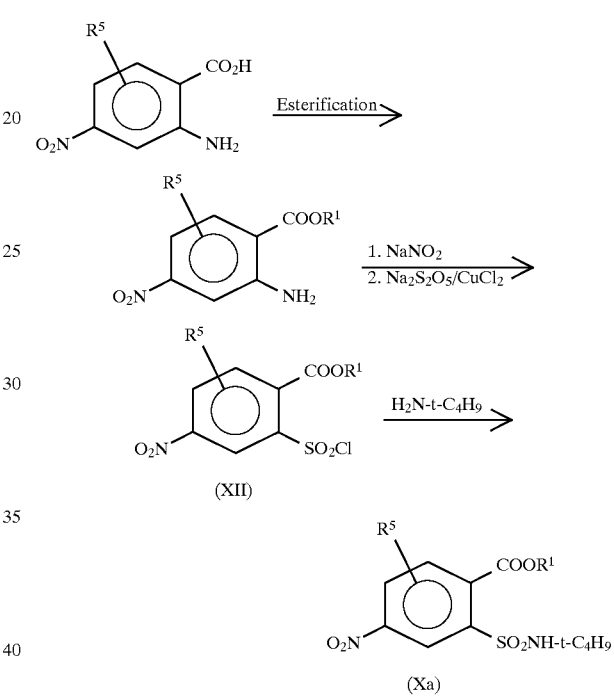

it being possible for all the reaction steps to be carried out by methods analogous to those known from the literature.

The compound (Xa; $R^1$=Me) is a suitable precursor for the preparation of the amides (Xb). They are likewise obtained by methods analogous to those known from the literature from (Xa) by reaction with the particular amine.

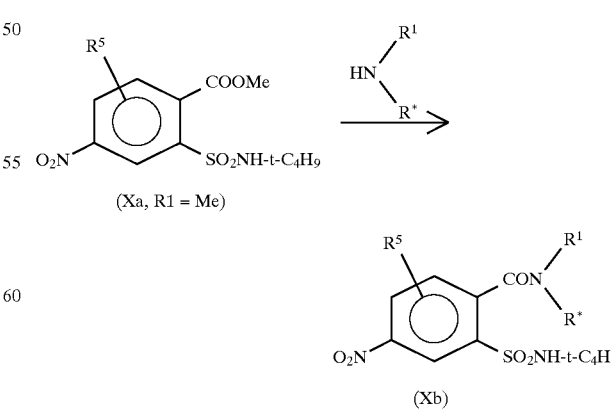

The compounds of the formula (II) can also be prepared in an analogous manner bypassing the t-butyl protective group (cf. EP 562 575). For this, a compound of the formula (XII) is reacted with ammonia instead of with t-butylamine and the subsequent procedure is as described for compound (X) or in EP 562 575.

The carbamates of the formula (III) can be prepared by methods which are described in South African Patent Applications 82/5671 and 82/5045 and EP-A 70804 (U.S. Pat. No. 4,480,101) or RD 275056.

The reaction of the compounds (IV) with the aminoheterocyclic compounds (V) is preferably carried out in inert, aprotic solvents, such as, for example, dioxane, acetonitrile or tetrahydrofuran, at temperatures between 0° C. and the boiling point of the solvent. The starting materials (V) required are known from the literature or can be prepared by processes known from the literature. The phenylsulfonyl-carbamates of the formula (VI) are obtained analogously to U.S. Pat. No. 4,684,393 or U.S. Pat. No. 4,743,290.

The phenylsulfonyl isocyanates of the formula (VI) can be prepared analogously to U.S. Pat. No. 4,481,029 and reacted with the amino-heterocyclic compounds (V).

The (thio)isocyanates of the formula (VII) are obtainable by processes known from the literature (EP-A-232067, EP-A-166516). The reaction of the (thio)isocyanate (VII) with compounds (II) is carried out at $-10°$ C. to $100°$ C., preferably $20°$ to $100°$ C., in an inert aprotic solvent, such as, for example, acetone or acetonitrile, in the presence of a suitable base, for example $N(C_2H_5)_3$ or $K_2CO_3$.

The reaction of an amino-heterocyclic compound of the formula (V) with diphenyl carbonate and a sulfonamide of the formula (II) in a one-pot reaction can be carried out in accordance with EP-A-562 575.

The salts of the compounds of the formula (I) are preferably prepared in inert polar solvents, such as, for example, water, methanol or acetone, at temperatures of $0°–100°$ C. Suitable bases for the preparation of the salts according to the invention are, for example, alkali metal carbonates, such as potassium carbonate, alkali metal and alkaline earth metal hydroxides, for example NaOH or KOH, or ammonia or ethanolamine.

The "inert solvents" mentioned in the above process variants mean in each case solvents which are inert under the particular reaction conditions but which do not have to be inert under any desired reaction conditions.

The compounds of the formula (I) according to the invention have an excellent herbicidal activity against a broad spectrum of economically important mono- and dicotyledon harmful plants. Perennial weeds which are difficult to control and shoot from rhizomes, rootstock or other permanent organs are also readily attacked by the active compounds. It is irrelevant here whether the substances are applied prior to sowing, pre-emergence or post-emergence.

Some representatives of monocotyledon and dicotyledon weed flora which can be controlled by the compounds according to the invention may be mentioned specifically by way of example, without a limitation to certain species being intended by the naming of these.

On the part of the monocotyledon species of weeds, for example, Avena, Lolium, Alopecurus, Phalaris, Echinochloa, Digitaria, Setaria and Cyperus species from the annual group and on the part of the perennial species, Agropyron, Cynodon, Imperata and Sorghum and also perennial Cyperus species are readily attacked.

In the case of dicotyledon species of weeds, the action spectrum extends to species such as, for example, Galium, Viola, Veronica, Lamium, Stellaria, Amaranthus, Sinapis, Ipomoea, Matricaria, Abutilon and Sida on the annual side, and Convolvulus, Cirsium, Rumex and Artemisia in the case of perennial weeds.

Weeds which occur under the specific growing conditions in rice, such as, for example, Sagittaria, Alisma, Eleocharis, Scirpus and Cyperus, are likewise controlled outstandingly by the active compounds according to the invention.

If the compounds according to the invention are applied to the soil surface before germination, either the emergence of the weed seedlings is prevented completely or the weeds grow to the cotyledon stage but then stop their growth and finally die completely at the end of three to four weeks.

If the active compounds are applied to the green parts of plants by the post-emergence method, a drastic stop in growth likewise occurs very rapidly after the treatment and the weed plants remain in the growth stage existing at the time of application or die completely after a certain period of time, so that weed competition, which is harmful to the crop plants, is eliminated very early and lastingly in this manner.

Although the compounds according to the invention have an excellent herbicidal activity against monocotyledon and dicotyledon weeds, crop plants of economically important crops, such as, for example, wheat, barley, rye, rice, maize, sugar beet, cotton and soya, are harmed only insignificantly or not at all. For these reasons, the present compounds are particularly suitable for selective control of undesirable plant growth in agricultural crop plantations.

The substances according to the invention furthermore have outstanding growth regulatory properties in crop plants. They intervene in the endogenous metabolism of the plants in a regulating manner and can therefore be employed for controlled influencing of plant contents and for facilitating harvesting, such as, for example, by inducing desiccation and stunted growth. They are furthermore also suitable for general control and inhibition of undesirable vegetative growth without killing the plants at the same time. Inhibition of vegetative growth plays a major rôle in many monocotyledon and dicotyledon crops, since lodging can be reduced or prevented completely by this means.

The compounds according to the invention can be used in the customary formulations in the form of wettable powders, emulsifiable concentrates, sprayable solutions, dusting powders or granules. The invention therefore also relates to herbicidal and plant growth-regulating compositions which comprise the compounds of the formula (I).

The compounds of the formula (I) can be formulated in various ways, depending on the biological and/or chemico-physical parameters which prevail. Suitable formulation possibilities are, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting powders (DP), seed dressings, granules for application by scattering and to the soil, granules (GR) in the form of microgranules, sprayed granules, absorption granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], Volume 7, C. Hauser Verlag Munich, 4th edition 1986, Wade van Valkenburg, "Pesticide Formulations", Marcel Dekker, N.Y., 1973; K. Martens, "Spray Drying", Handbook, 3rd edition 1979, G. Goodwin Ltd. London.

The necessary formulating auxiliaries, such as inert materials, surfactants, solvents and further additives, are likewise known and are described, for example, in: Watkins, "Handbook of Insecticide Dust Diluents and Carriers", 2nd edition, Darland Books, Caldwell N.J., H.v. Olphen, "Introduction to Clay Colloid Chemistry"; 2nd edition, J. Wiley & Sons, N.Y.; C. Marsden, "Solvents Guide"; 2nd edition, Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical technology], Volume 7, C. Hauser Verlag Munich, 4th edition 1986.

Combinations with other substances having a pesticidal action, such as, for example, insecticides, acaricides, herbicides and fungicides, and with safeners, fertilizers and/or growth regulators, can be prepared on the basis of these formulations, for example in the form of a ready-to-use formulation or as a tank mix.

Wettable powders are preparations which are uniformly dispersible in water and which, alongside the active compound, and in addition to a diluent or inert substance, also comprise surfactants of an ionic and/or nonionic nature (wetting agents, dispersing agents), for example polyoxyethylated alkylphenols, polyoxyethylated fatty alcohols, polyoxyethylated fatty amines, fatty alcohol polyglycol ether-sulfates, alkanesulfonates, alkylbenzenesulfonates, sodium ligninsulfonate, sodium 2,2'-dinaphthylmethane-6, 6'-disulfonate, sodium dibutylnaphthalene-sulfonate or sodium oleoylmethyltauride. To prepare the wettable powders, for example, the herbicidal active compounds are finely ground in customary apparatuses, such as hammer mills, blast mills and air jet mills, and are mixed with the formulating auxiliaries at the same time or subsequently.

Emulsifiable concentrates are prepared by dissolving the active compound in an organic solvent, for example butanol, cyclohexanone, dimethylformamide, xylene or also higher-boiling aromatics or hydrocarbons or mixtures of organic solvents, with the addition of one or more surfactants of an ionic and/or nonionic nature (emulsifiers). Emulsifiers which can be used are, for example: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dusting powders are obtained by grinding the active compound with finely divided solid substances, for example talc, naturally occurring clays, such as kaolin, bentonite and pyrophyllite, or diatomaceous earth.

Suspension concentrates can be water- or oil-based. They can be prepared, for example, by wet grinding by means of commercially available bead mills and, if appropriate, with the addition of surfactants, such as are already listed above, for example, for the other types of formulation.

Emulsions, for example oil-in-water emulsions (EW), can be prepared, for example, by means of stirrers, colloid mills and/or static mixers using aqueous organic solvents and if appropriate surfactants, such as are already listed above, for example, for the other types of formulation.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

Water-dispersible granules are as a rule prepared by customary processes, such as spray drying, fluidized bed granulation, disk granulation, mixing with high-speed mixers and extrusion, without a solid inert material.

For the preparation of disk, fluidized bed, extruder and sprayed granules cf., for example, processes in "Spray-drying Handbook" 3rd edition 1979. G. Goodwin Ltd., London; J. E. Browning, "Agglomeration", Chemical and Engineering 1967, pages 147 et seq.; "Perry's Chemical Engineer's Handbook", 5th edition, McGraw-Hill, New York 1973, pages 8–57.

For further details on the formulation of plant protection agents cf., for example, G. C. Klingman, "Weed Control as a Science", John Wiley and Sons, Inc., New York, 1961, pages 81–96 and J. D. Freyer, S. A. Evans, "Weed Control Handbook", 5th edition, Blackwell Scientific Publications, Oxford, 1968, pages 101–103.

The agrochemical formulations as a rule comprise 0.1 to 99% by weight, in particular 0.1 to 95% by weight, of active compound of the formula (I). In wettable powders, the active compound concentration is, for example, about 10 to 90% by weight, the remainder to make up 100% by weight comprising customary formulation constituents. In emulsifiable concentrates, the active compound concentration can be about 1 to 90, preferably 5 to 80% by weight. Dust-like formulations comprise 1 to 30% by weight of active compound, preferably usually 5 to 20% by weight of active compound, and sprayable solutions comprise about 0.05 to 80, preferably 2 to 50% by weight of active compound. In water-dispersible granules, the active compound content partly depends on whether the active compound is present in liquid or solid form and which granulating auxiliaries, fillers and the like are used. In water-dispersible granules, the content of active compound is, for example, between 1 and 95% by weight, preferably between 10 and 80% by weight.

In addition, the active compound formulations mentioned comprise, if appropriate, the particular customary tackifiers, wetting agents, dispersing agents, emulsifiers, penetration agents, preservatives, antifreezes and solvents, fillers, carrier substances and dyestuffs, defoamers, evaporation inhibitors and agents which influence the pH and viscosity.

Known active compounds such as are described, for example, in Weed Research 26, 441–445 (1986), or "The Pesticide Manual", 9th edition, The British Crop Protection Council, 1990/91, Bracknell, England, and literature mentioned therein can be employed as combination partners for the active compounds according to the invention in mixture formulations or in a tank mix. The following active compounds may be mentioned, for example, as herbicides which are known from the literature and can be combined with the compounds of the formula (I) (Note: The compounds are named either with the "common name" according to the International Organization for Standardization (ISO) or with the chemical name, if appropriate together with a customary code number): acetochlor; acifluorfen; aclonifen; AKH 7088, i.e. [[[1-[5-[2-chloro-4-(trifluoromethyl)phenoxy]-2-nitro-phenyl]-2-methoxyethylidene]amino]oxy]acetic acid and -acetic acid methyl ester; alachlor; alloxydim; ametryn; amidosulfuron; amitrol; AMS, i.e. ammonium sulfamate; anilofos; asulam; atrazin; azimsulfurone (DPX-A8947); aziprotryn; barban; BAS 516 H, i.e. 5-fluoro-2-phenyl-4H-

3,1-benzoxazin-4-one; benazolin; benfluralin; benfuresate; bensulfuron-methyl; bensulide; bentazone; benzofenap; benzofluor; benzoyl-prop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. diethyldithiocarbamic acid 2-chloroallyl ester; chlomethoxyfen; chloramben; chlorazifop-butyl, chlormesulon (ICI-A0051); chlorbromuron; chlorbufam; chlorfenac; chlorflurecolmethyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and ester derivatives thereof (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and ester derivatives thereof (for example butyl ester, DEH-112); cyperguat; cyprazine; cyprazole; daimuron; 2,4-DB; dalapon; desmedipham; desmetryn; di-allate; dicamba; dichlobenil; dichlorprop; diclofop and esters thereof, such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]-phenyl] ethanesulfonamide; ethoxyfen and esters thereof (for example ethyl ester, HN-252); etobenzanid (HW 52); fenoprop; fenoxan, fenoxaprop and fenoxaprop-P and esters thereof, for example fenoxaprop-P-ethyl and fenoxapropethyl; fenoxydim; fenuron; flamprop-methyl; flazasulfuron; fluazifop and fluazifop-P and esters thereof, for example fluazifop-butyl and fluazifop-P-butyl; fluchloralin; flumetsulam; flumeturon; flumiclorac and esters thereof (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosaten; halosulfuron and esters thereof (for example methyl ester, NC-319); haloxyfop and esters thereof; haloxyfop-P (=R-haloxyfop) and esters thereof; hexazinone; imazamethabenz-methyl; imazapyr; imazaquin and salts, such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and esters thereof; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and esters thereof (for example propargyl ester); quinclorac; quinmerac; quinofop and ester derivatives thereof, quizalofop and quizalofop-P and ester derivatives thereof, for example quizalofopethyl; quizalofop-P-tefuryl and -ethyl; renriduron; rimsulfuron (DPX-E-9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)-phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluoron; thizopyr (Mon-13200); thidiazimin (SN-124085); thifensulfuronmethyl; thiobencarb; tiocarbazil; tralkoxydim; triallate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82–556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations in the commercially available form are diluted in the customary manner, if appropriate, for example by means of water in the case of wettable powders, emulsifiable concentrates, dispersions and water-dispersible granules. Dust-like formulations, soil or scattering granules and sprayable solutions are usually not diluted further with additional inert substances before use.

The required amount of compounds of the formula (I) to be applied varies with the outdoor conditions, such as temperature and humidity, the nature of the herbicide used and the like. It can vary within wide limits, for example between 0.001 and 10.0 kg/ha or more of active substance, but is preferably between 0.005 and 5 kg/ha.

A. CHEMICAL EXAMPLES

A1. Methyl 4-amino-2-(N-tert-butylsulfamoyl)benzoate 50.0 g (0.158 mol) of methyl 2-(N-tert-butylsulfamoyl)-4-nitrobenzoate (prepared in accordance with DE-A 4 236 902) are added to a mixture of 180 ml of acetic acid and 75 ml of water and the mixture is heated to 80° C. 26.5 g (0.474 mol) of iron powder are added in portions such that the temperature does not rise above 85° C. The mixture is then stirred at 80° C. for 4 hours, 85 ml of 2N HCl are added at this temperature and the mixture is allowed to cool to 25° C. The solid is filtered off and washed thoroughly with water. It is then extracted hot 3 times with 250 ml of ethyl acetate each time. The ethyl acetate phase is evaporated and the residue is triturated with diisopropyl ether and dried. 37.7 g (83% of theory) of methyl 4-amino-2-(N-tert-utylsulfamoyl) benzoate of melting point 198°–199° C. are obtained.

A2. Methyl 2-(N-tert-butylsulfamoyl)-4-hydrazinobenzoate 25.0 g (0.087 mol) of methyl 4-amino-2-(N-tert-butylsulfamoyl)benzoate are suspended in a mixture of 150 ml of concentrated HCl and 130 ml of water. A solution of 7.8 g (0.114 mol) of sodium nitrite is added dropwise at 0°–5° C. A small amount of undissolved constituents are filtered off cold and the still cold diazonium salt solution is allowed to run slowly at 0° C. into a suspension of 55.0 g (0.244 mol) of $SnCl_2.2H_2O$ in 55 ml of concentrated HCl. The mixture is subsequently stirred for 30 minutes and is then left to stand for 15 hours, while cooling with ice. Most of the HCl is first neutralized by addition of 6N NaOH and the pH is then brought to about 6 with solid $NaHCO_3$. The mixture is extracted several times with ethyl acetate, the extracts are dried and the solvent is removed in vacuo. After trituration of the residue with diisopropyl ether and drying, 18.3 g (70% of theory) of methyl 2-(N-tert-butylsulfamoyl)-4-hydrazinobenzoate of melting point 133°–136° C. are obtained.

A3. Methyl 2-(N-tert-butylsulfamoyl)-4-(2-isobutyrylhydrazino)benzoate 2.2 g (0.021 mol) of isobutyryl chloride are added to 6.0 g (0.02 mol) of methyl 2-(N-tert-butylsulfamoyl)-4-hydrazinobenzoate in 50 ml of pyridine at −30° C. The mixture is subsequently stirred at this temperature for 2 hours and allowed to come to room temperature, 200 ml of $CH_2Cl_2$ are added, and the mixture is washed successively with water, 2N HCl and water, dried and evaporated. Trituration of the residue with diisopropyl ether, filtration with suction and drying gives 4.0 g (54% of theory) of methyl 2-(N-tert-butylsulfamoyl)-4-isobutyrylhydrazino)benzoate with the following nuclear magnetic resonance data:

$^1$H-NMR ($d_6$-DMSO): δ=1.09 (d, 6H, $C(CH_3)_2$; 1.14 (s, 9H, t-$C_4H_9$); 2.50 (m, 1H, CH); 3.80 (s, 3H, $OCH_3$); 6.82 (s, 1H, $SO_2NH$); 6.82 (dd, 1H, ArH); 7.31 (d, 1H, ArH); 7.67 (d, 1H, ArH); 8.69 (s, 1H, NH); 9.95 (s, 1H, NH).

A4. Methyl 2-(N-tert-butylsulfamoyl)-4-(2-phenylacetylhydrazino)benzoate 1.5 g (7.3 mmol) of dicyclohexylcarbodiimide (DCC) are added to a solution of 2.0 g (6.6 mmol) of methyl 2-(N-tert-butylsulfamoyl)-4-hydrazinobenzoate, 0.9 g (6.6 mmol) of phenylacetic acid and 0.03 g of 4-dimethylaminopyridine (DMAP) in 20 ml of $CH_2Cl_2$ at 0° C. The mixture is stirred at 25° C. for 15 hours, the solid is filtered off with suction and the organic phase is washed successively with water, 1N HCl and $NaHCO_3$ solution, dried and evaporated. This gives 1.6 g (58% of theory) of methyl 2-(N-tert-butylsulfamoyl)-4-(2-phenylacetyl-hydrazino)benzoate with the following nuclear magnetic resonance data:

$^1$H-NMR ($d_6$-DMSO): δ=1.13 (s, 9H, t-$C_4H_9$); 3.54 (s, 2H, $CH_2$); 3.79 (s, 3H, $OCH_3$); 6.79 (dd, 1H, ArH); 6.88 (s, 1H, $SO_2NH$); 7.20–7.36 (m, 6H, ArH); 7.62 (d, 1H, ArH); 8.78 (s, 1H, NH); 10.15 (s, 1H, NH).

A5. Methyl 4-(2-isobutyrylhydrazino)-2-sulfamoylbenzoate 1.0 g (2.7 mmol) of methyl 2-(N-tert-butylsulfamoyl)-4-(2-isobutyrylhydrazino)benzoate is stirred in 10 ml of trifluoroacetic acid at 25° C. for 2 hours. The mixture is evaporated and the residue is triturated with diethyl ether. Filtration with suction and drying gives 0.8 g (94% of theory) of methyl 4-(2-isobutyrylhydrazino)-2-sulfamoylbenzoate of melting point 198°–200° C.

A6. Methyl 2-[3-(4,6-dimethoxypyrimidin-2-yl)ureidosulfonyl]-4-(2-isobutyrylhydrazino)benzoate 0.8 g (2.5 mmol) of methyl 4-(2-isobutyrylhydrazino)-2-sulfamoylbenzoate and 0.77 g (2.8 mmol) of phenyl-N-(4,6-dimethoxypyrimidin-2-yl)carbamate are initially introduced into 25 ml of acetonitrile. 0.83 g (5.6 mmol) of 1,8-diazabicyclo[5.4.0]undec-7-ene (DBU) is added dropwise at 0° C. and the mixture is stirred at this temperature for 2 hours. It is poured into water and the pH is brought to 2–3 with 2N HCl. The aqueous phase is extracted three times with $CH_2Cl_2$. After the $CH_2Cl_2$ phase has been washed with 2N HCl and water, it is dried and evaporated. The residue is triturated with diethyl ether. Filtration with suction and drying gives 0.8 g (64% of theory) of methyl 2-[3-(4,6-dimethoxypyrimidin-2-yl)-ureidosulfonyl]-4-(2-isobutyrylhydrazino)benzoate of melting point 169°–171° C. (decomposition).

The compounds described in Tables 1 to 5 are obtained analogously to Examples A1–A6. In the tables:

Ex.=Example m.p.=Solidification point (melting point) in °C.

Me=Methyl

Et=Ethyl

Pr=n-Propyl i-Pr=Isopropyl c-Pr=Cyclopropyl

Bu=n-Butyl

Ph=Phenyl

Allyl=$CH_2CH=CH_2$ (d)=(decomp.)=melting point with decomposition

TABLE 1

Compounds of the formula (Ia)

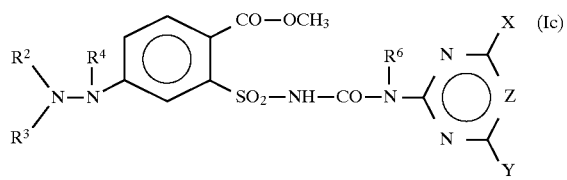

| Ex. no. | $R^2$ | $R^3$ | $R^4$ | $R^6$ | X | Y | Z | m.p. [°C.] |
|---|---|---|---|---|---|---|---|---|
| 1 | CHO | H | H | H | OMe | OMe | CH | |
| 2 | " | " | " | " | " | Me | CH | |
| 3 | " | " | " | " | " | OMe | N | |
| 4 | " | " | " | " | " | Me | " | |
| 5 | " | " | " | " | " | Cl | CH | |
| 6 | " | " | " | " | " | Me | Me | " |

TABLE 1-continued

Compounds of the formula (Ia)

| Ex. no. | R² | R³ | R⁴ | R⁶ | X | Y | Z | m.p. [°C.] |
|---|---|---|---|---|---|---|---|---|
| 7 | " | " | " | " | OCH₂CF₃ | NMe₂ | N | |
| 8 | " | " | " | " | CF₃ | OMe | " | |
| 9 | " | " | " | " | OCHF₂ | OCHF₂ | CH | |
| 10 | " | " | " | Me | OMe | OMe | " | |
| 11 | " | " | " | " | " | Me | N | |
| 12 | COMe | " | " | H | " | OMe | CH | 158–60 (decomp.) |
| 13 | " | " | " | " | " | Me | " | |
| 14 | " | " | " | " | " | OMe | N | 116–19 (d)**] |
| 15 | " | " | " | " | " | Me | " | 135–38 (d)**] |
| 16 | " | " | " | " | " | Cl | CH | 115–18 (d)**] |
| 17 | COMe | H | H | H | Me | Me | CH | |
| 18 | " | " | " | " | OCH₂CF₃ | NMe₂ | N | |
| 19 | " | " | " | " | CF₃ | OMe | N | |
| 20 | " | " | " | " | OCHF₂ | OCHF₂ | CH | |
| 21 | " | " | " | Me | OMe | OMe | " | |
| 22 | " | " | " | " | " | Me | N | |
| 23 | " | " | " | H | OEt | OMe | CH | |
| 24 | " | " | " | " | SMe | OMe | CH | |
| 25 | COMe | H | H | H | Me | Cl | CH | |
| 26 | " | " | " | " | OEt | OMe | N | |
| 27 | " | " | " | " | OMe | Et | " | |
| 28 | " | " | " | " | OEt | NHMe | N | |
| 29 | " | " | " | " | CF₃ | OMe | CH | |
| 30 | " | " | " | Et | OMe | OMe | " | |
| 31 | " | " | " | " | " | Me | " | |
| 32 | " | " | " | " | " | OMe | N | |
| 33 | " | " | " | " | " | Me | " | |
| 34 | " | " | " | " | " | Cl | CH | |
| 35 | " | " | " | " | Me | Me | CH | |
| 36 | " | " | " | " | OCH₂CF₃ | NMe₂ | N | |
| 37 | " | " | " | " | CF₃ | OMe | N | |
| 38 | " | " | " | " | OCHF₂ | OCHF₂ | CH | |
| 39 | " | Me | Me | Me | OMe | OMe | CH | |
| 40 | " | " | " | " | " | Me | N | |
| 41 | " | " | " | H | " | OMe | CH | |
| 42 | " | " | " | " | OMe | Me | N | |
| 43 | COMe | Et | H | H | OMe | OMe | CH | |
| 44 | " | " | " | " | " | Me | N | |
| 45 | " | " | " | Me | " | OMe | CH | |
| 46 | " | " | " | " | " | Me | N | |
| 47 | " | Me | " | H | " | OMe | CH | 138–40 (d)**] |
| 48 | " | " | " | " | " | Me | N | |
| 49 | " | H | Me | " | " | OMe | CH | |
| 50 | " | " | " | " | " | Me | N | |
| 51 | " | Me | " | H | " | OMe | CH | |
| 52 | " | " | " | " | " | Me | N | |
| 53 | " | Allyl | H | " | " | OMe | CH | |
| 54 | " | " | " | " | " | Me | N | |
| 55 | " | H | CH₂C≡CH | " | " | OMe | CH | |
| 56 | " | " | " | " | " | Me | N | |
| 57 | " | Cl(CH₂)₂ | H | " | " | OMe | CH | |
| 58 | " | " | " | " | " | Me | H | |
| 59 | " | MeO(CH₂)₂ | " | " | " | OMe | CH | |
| 60 | " | " | " | " | " | Me | N | |
| 61 | " | H | CH₂CH₂SMe | " | " | OMe | CH | |
| 62 | " | " | " | " | " | Me | N | |
| 63 | " | CH₂Ph | H | " | " | OMe | CH | |
| 64 | " | " | " | " | " | Me | N | |
| 65 | " | H | CH₂COOMe | " | " | OMe | CH | |

TABLE 1-continued

Compounds of the formula (Ia)

| Ex. no. | R² | R³ | R⁴ | R⁶ | X | Y | Z | m.p. [°C.] |
|---|---|---|---|---|---|---|---|---|
| 66 | " | " | H | " | " | Me | N | |
| 67 | " | COMe | " | " | " | OMe | CH | |
| 68 | COMe | H | H | H | OMe | Me | N | |
| 69 | " | " | COMe | " | " | OMe | CH | |
| 70 | " | " | H | " | " | Me | N | |
| 71 | " | COMe | COMe | " | " | OMe | CH | 151–54 (d)**] |
| 72 | " | H | H | CONHEt | " | Me | N | |
| 73 | " | " | " | " | " | OMe | CH | |
| 74 | " | " | " | CONHEt | " | Me | N | |
| 75 | COEt | " | H | " | " | OMe | CH | 138–41 |
| 76 | " | " | " | " | " | Me | CH | |
| 77 | " | " | " | " | " | OMe | N | |
| 78 | " | " | " | " | " | Me | N | |
| 79 | " | " | " | " | " | Cl | CH | |
| 80 | " | " | " | " | Me | Me | CH | |
| 81 | " | " | " | " | OCH₂CF₃ | NMe₂ | N | |
| 82 | " | " | " | " | CF₃ | OMe | " | |
| 83 | " | " | " | " | OCHF₂ | OCHF₂ | CH | |
| 84 | " | " | " | Me | OMe | OMe | " | |
| 85 | " | " | " | " | " | Me | N | |
| 86 | COPr | " | " | H | " | OMe | CH | |
| 87 | " | " | " | " | " | Me | " | |
| 88 | " | " | " | " | " | OMe | N | |
| 89 | " | " | " | " | " | Me | N | |
| 90 | " | " | " | " | " | Cl | CH | |
| 91 | " | " | " | " | Me | Me | CH | |
| 92 | " | " | " | " | OCH₂CF₃ | NMe₂ | N | |
| 93 | COPr | H | H | H | CF₃ | OMe | N | |
| 94 | " | " | " | Me | OCHF₂ | OCHF₂ | CH | |
| 95 | " | " | " | " | OMe | OMe | " | |
| 96 | " | " | " | H | " | Me | N | |
| 97 | COBu | " | " | " | " | OMe | CH | |
| 98 | " | " | " | " | " | Me | CH | |
| 99 | " | " | " | " | " | OMe | N | |
| 100 | " | " | " | " | " | Me | " | |
| 101 | " | " | " | " | " | Cl | CH | |
| 102 | " | " | " | " | Me | Me | CH | |
| 103 | " | " | " | " | OCH₂CF₃ | NMe₂ | N | |
| 104 | " | " | " | " | CF₃ | OMe | N | |
| 105 | " | " | " | " | OCHF₂ | OCHF₂ | CH | |
| 106 | " | " | " | Me | OMe | OMe | " | |
| 107 | " | " | " | " | " | Me | N | |
| 108 | CO-i-Pr | " | " | H | " | OMe | CH | 169–71 (d)**] |
| 109 | " | " | " | " | " | Me | " | |
| 110 | " | " | " | " | " | OMe | N | 94–97 (d)**] |
| 111 | " | " | " | " | " | Me | " | 142–45 (d)**] |
| 112 | " | " | " | " | " | Cl | CH | 165–68 (d)**] |
| 113 | " | " | " | " | Me | Me | " | |
| 114 | " | " | " | " | OCH₂CF₃ | NMe₂ | N | |
| 115 | " | " | " | " | CF₃ | OMe | " | |
| 116 | " | " | " | " | OCHF₂ | OCHF₂ | CH | |
| 117 | " | " | " | Me | OMe | OMe | " | |
| 118 | CO-i-Pr | H | H | Me | OMe | Me | N | |
| 119 | CO-c-Pr | " | " | H | " | OMe | CH | 123–25 (d)**] |
| 120 | " | " | " | " | " | Me | CH | |
| 121 | " | " | " | " | " | OMe | N | |
| 122 | " | " | " | " | " | Me | N | |
| 123 | " | " | " | " | " | Cl | CH | |
| 124 | " | " | " | " | " | Me | " | |

TABLE 1-continued

Compounds of the formula (Ia)

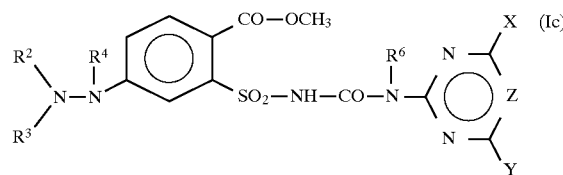

| Ex. no. | R² | R³ | R⁴ | R⁶ | X | Y | Z | m.p. [°C.] |
|---|---|---|---|---|---|---|---|---|
| 125 | " | " | " | " | OCH₂CF₃ | NMe₂ | N | |
| 126 | " | " | " | " | CF₃ | OMe | N | |
| 127 | " | " | " | " | OCHF₂ | OCHF₂ | CH | |
| 128 | " | " | " | Me | OMe | OMe | CH | |
| 129 | " | " | " | " | " | Me | N | |
| 130 | COC(CH₃)₃ | " | " | H | " | OMe | CH | 125–28 (d)**] |
| 131 | " | " | " | " | " | Me | " | |
| 132 | " | " | " | " | " | OMe | N | |
| 133 | " | " | " | " | " | Me | " | |
| 134 | " | " | " | " | " | Cl | CH | |
| 135 | " | " | " | " | Me | Me | " | |
| 136 | " | " | " | " | OCH₂CF₃ | NMe₂ | N | |
| 137 | " | " | " | " | CF₃ | OMe | N | |
| 138 | " | " | " | " | OCHF₂ | OCHF₂ | CH | |
| 139 | " | " | " | Me | OMe | OMe | " | |
| 140 | " | " | " | " | OMe | Me | N | |
| 141 | COCH₂Cl | " | " | H | " | OMe | CH | |
| 142 | " | " | " | " | " | Me | " | |
| 143 | COCH₂Cl | H | H | H | OMe | OMe | N | |
| 144 | " | " | " | " | " | Me | N | |
| 145 | " | " | " | " | " | Cl | CH | |
| 146 | " | " | " | " | Me | Me | " | |
| 147 | " | " | " | " | OCH₂CF₃ | NMe₂ | N | |
| 148 | " | " | " | " | CF₃ | OMe | " | |
| 149 | " | " | " | " | OCHF₂ | OCHF₂ | CH | |
| 150 | " | " | " | Me | OMe | OMe | CH | |
| 151 | " | " | " | " | " | Me | N | |
| 152 | COCHCl₂ | " | " | H | " | OMe | CH | |
| 153 | " | " | " | " | " | Me | " | |
| 154 | " | " | " | " | " | OMe | N | |
| 155 | " | " | " | " | " | Me | " | |
| 156 | " | " | " | " | " | Cl | CH | |
| 157 | " | " | " | " | Me | Me | " | |
| 158 | " | " | " | " | OCH₂CF₃ | NMe₂ | N | |
| 159 | " | " | " | " | CF₃ | OMe | " | |
| 160 | " | " | " | " | OCHF₂ | OCHF₂ | CH | |
| 161 | " | " | " | Me | OMe | OMe | " | |
| 162 | " | " | " | " | " | Me | N | |
| 163 | COCCl₃ | " | " | H | " | OMe | CH | |
| 164 | " | " | " | " | " | Me | " | |
| 165 | " | " | " | " | " | OMe | N | |
| 166 | " | " | " | " | " | Me | " | |
| 167 | " | " | " | " | " | Cl | CH | |
| 168 | " | " | " | " | Me | Me | " | |
| 169 | COCCl₃ | H | H | H | OCH₂CF₃ | NMe₂ | N | |
| 170 | " | " | " | " | CF₃ | OMe | " | |
| 171 | " | " | " | " | OCHF₂ | OCHF₂ | CH | |
| 172 | " | " | " | Me | OMe | OMe | CH | |
| 173 | " | " | " | " | " | Me | N | |
| 174 | COCF₃ | " | " | H | " | OMe | CH | |
| 175 | " | " | " | " | " | Me | " | |
| 176 | " | " | " | " | " | OMe | N | |
| 177 | " | " | " | " | " | Me | N | |
| 178 | " | " | " | " | OMe | Cl | CH | |
| 179 | " | " | " | " | Me | Me | CH | |
| 180 | " | " | " | " | OCH₂CF₃ | NMe₂ | N | |
| 181 | " | " | " | " | CF₃ | OMe | " | |
| 182 | " | " | " | " | OCHF₂ | OCHF₂ | CH | |
| 183 | CO(CH₂)₇Me | " | " | " | OMe | OMe | CH | 110–12 |
| 184 | " | " | " | " | " | Me | N | |
| 185 | COPh | " | " | " | " | OMe | CH | 124–28 |
| 186 | " | " | " | " | " | Me | CH | |
| 187 | " | " | " | " | " | OMe | N | |
| 188 | " | " | " | " | " | Me | " | |

TABLE 1-continued

Compounds of the formula (Ia)

| Ex. no. | R² | R³ | R⁴ | R⁶ | X | Y | Z | m.p. [°C.] |
|---|---|---|---|---|---|---|---|---|
| 189 | " | " | " | " | " | Cl | CH | |
| 190 | " | " | " | " | Me | Me | " | |
| 191 | " | " | " | " | OCH₂CF₃ | NMe₂ | N | |
| 192 | " | " | " | " | CF₃ | OMe | " | |
| 193 | " | " | " | " | OCHF₂ | OCHF₂ | CH | |
| 194 | " | " | " | Me | OMe | OMe | " | |
| 195 | COPh | H | H | Me | OMe | Me | N | |
| 196 | CO(4-Cl)C₆H₄ | " | " | H | " | OMe | CH | |
| 197 | " | " | " | " | " | Me | N | |
| 198 | CO(4-Me)C₆H₄ | " | " | " | " | OMe | CH | |
| 199 | " | " | " | " | " | Me | N | |
| 200 | CO(3-CF₃)C₆H₄ | " | " | " | " | OMe | CH | |
| 201 | " | " | " | " | " | Me | N | |
| 202 | CO-cyclopentyl | " | " | " | " | OMe | CH | 118–20 (d)**] |
| 203 | " | " | " | " | " | Me | N | |
| 204 | CO-2-furyl | " | " | " | " | OMe | CH | 128–30 |
| 205 | " | " | " | " | " | Me | N | |
| 206 | CO-2-thienyl | " | " | " | OMe | OMe | CH | 128–30 (d)**] |
| 207 | " | " | " | " | " | Me | N | |
| 208 | CO-3-pyridyl | " | " | " | " | OMe | CH | |
| 209 | " | " | " | " | " | Me | N | |
| 210 | CO(CH₂)₃Cl | " | " | " | " | OMe | CH | 123–26 (d)**] |
| 211 | " | " | " | " | " | Me | " | |
| 212 | " | " | " | " | " | OMe | N | |
| 213 | " | " | " | " | " | Me | N | |
| 214 | " | " | " | " | " | Cl | CH | |
| 215 | " | " | " | " | Me | Me | CH | |
| 216 | " | " | " | " | OCH₂CF₃ | NMe₂ | N | |
| 217 | CO(CH₂)₃Cl | H | H | H | CF₃ | OMe | N | |
| 218 | " | " | " | " | OCHF₂ | OCHF₂ | CH | |
| 219 | " | " | " | Me | OMe | OMe | " | |
| 220 | " | " | " | " | " | Me | N | |
| 221 | COCH=CH₂ | " | " | H | " | OMe | CH | 128–30 (d)**] |
| 222 | " | " | " | " | " | Me | " | |
| 223 | " | " | " | " | " | OMe | N | |
| 224 | " | " | " | " | " | Me | " | |
| 225 | " | " | " | " | " | Cl | CH | |
| 226 | " | " | " | " | Me | Me | " | |
| 227 | " | " | " | " | OCH₂CF₃ | NMe₂ | N | |
| 228 | " | " | " | " | CF₃ | OMe | N | |
| 229 | " | " | " | " | OCHF₂ | OCHF₂ | CH | |
| 230 | " | " | " | Me | OMe | OMe | " | |
| 231 | " | " | " | " | " | Me | N | |

TABLE 1-continued

Compounds of the formula (Ia)

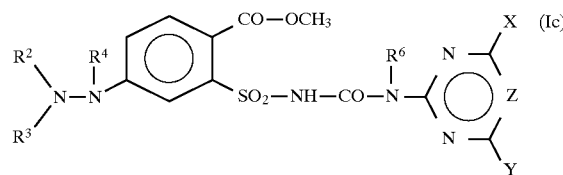

| Ex. no. | $R^2$ | $R^3$ | $R^4$ | $R^6$ | X | Y | Z | m.p. [°C.] |
|---|---|---|---|---|---|---|---|---|
| 232 | COC≡CH | " | " | H | OMe | OMe | CH | |
| 233 | " | " | " | " | " | Me | " | |
| 234 | " | " | " | " | " | OMe | N | |
| 235 | " | " | " | " | " | Me | " | |
| 236 | " | " | " | " | " | Cl | CH | |
| 237 | " | " | " | " | Me | Me | " | |
| 238 | " | " | " | " | OCH$_2$—CF$_3$ | NMe$_2$ | N | |
| 239 | " | " | " | " | CF$_3$ | OMe | N | |
| 240 | " | " | " | " | OCHF$_2$ | OCHF$_2$ | CH | |
| 241 | " | " | " | Me | OMe | OMe | " | |
| 242 | COC=CH | H | H | Me | OMe | Me | N | |
| 243 | COC(Me)=CH$_2$ | " | " | H | " | OMe | CH | |
| 244 | " | " | " | " | " | Me | | |
| 245 | COCH=CHCl | " | " | " | " | OMe | CH | |
| 246 | " | " | " | " | " | Me | N | |
| 247 | COCH$_2$OMe | " | " | " | " | OMe | CH | 206–09 (d)** |
| 248 | " | " | " | " | " | Me | N | |
| 249 | COCH$_2$SMe | " | " | " | " | OMe | CH | |
| 250 | " | " | " | " | " | Me | N | |
| 251 | CO(CH$_2$)$_2$CO$_2$Me | " | " | " | " | OMe | CH | |
| 252 | " | " | " | " | " | Me | N | |
| 253 | COCO$_2$Me | " | " | " | " | OMe | CH | 145–50 (d)** |
| 254 | " | " | " | " | " | Me | CH | |
| 255 | " | " | " | " | " | OMe | N | |
| 256 | " | " | " | " | " | Me | N | |
| 257 | " | " | " | " | " | Cl | CH | |
| 258 | " | " | " | " | Me | Me | CH | |
| 259 | " | " | " | " | OCH$_2$CF$_3$ | NMe$_2$ | N | |
| 260 | " | " | " | " | CF$_3$ | OMe | N | |
| 261 | " | " | " | " | OCHF$_2$ | OCHF$_2$ | CH | |
| 262 | " | " | " | Me | OMe | OMe | CH | |
| 263 | " | " | " | " | " | Me | N | |
| 264 | COCO$_2$Et | " | " | H | " | OMe | CH | |
| 265 | " | " | " | " | " | Me | N | |
| 266 | COCH$_2$Ph | H | H | H | OMe | OMe | CH | 126–28 (d)** |
| 267 | " | " | " | " | " | Me | CH | |
| 268 | " | " | " | " | " | OMe | N | |
| 269 | " | " | " | " | " | Me | N | |
| 270 | " | " | " | " | " | Cl | CH | |
| 271 | " | " | " | " | Me | Me | CH | |
| 272 | " | " | " | " | OCH$_2$CF$_3$ | NMe$_2$ | N | |
| 273 | " | " | " | " | CF$_3$ | OMe | N | |
| 274 | " | " | " | " | OCHF$_2$ | OCHF$_2$ | CH | |
| 275 | " | " | " | Me | OMe | OMe | CH | |
| 276 | " | " | " | " | " | Me | N | |
| 277 | " | " | " | H | OEt | OMe | CH | |
| 278 | " | " | " | " | SMe | " | CH | |
| 279 | " | " | " | " | Me | Cl | CH | |
| 280 | " | " | " | " | OEt | OMe | N | |
| 281 | " | " | " | " | OMe | Et | N | |
| 282 | " | " | " | " | OEt | NHMe | N | |
| 283 | " | " | " | " | CF$_3$ | OMe | CH | |
| 284 | COCH$_2$(2-F)C$_6$H$_4$ | " | " | " | OMe | " | CH | |
| 285 | " | " | " | " | " | Me | N | |
| 286 | COCH$_2$(3-F)C$_6$H$_4$ | " | " | " | " | OMe | CH | |
| 287 | " | " | " | " | " | Me | N | |
| 288 | COCH$_2$(4-F)C$_6$H$_4$ | " | " | " | " | OMe | CH | |
| 289 | " | " | " | " | " | Me | N | |
| 290 | COCH$_2$(2-Cl)C$_6$H$_4$ | " | " | " | " | OMe | CH | |
| 291 | COCH$_2$(2-Cl)C$_6$H$_4$ | H | H | H | OMe | Me | N | |
| 292 | COCH$_2$(3-Cl)C$_6$H$_4$ | " | " | " | " | OMe | CH | 132–34 |

TABLE 1-continued

Compounds of the formula (Ia)

[Structure (Ic): methyl benzoate with R²R³N-NR⁴- substituent and -SO₂-NH-CO-N(R⁶)- linked to a pyrimidine/triazine ring with X, Y, Z substituents]

| Ex. no. | R² | R³ | R⁴ | R⁶ | X | Y | Z | m.p. [°C.] |
|---|---|---|---|---|---|---|---|---|
| | | | | | | | | (d)**] |
| 293 | " | " | " | " | " | Me | N | |
| 294 | COCH₂(4-Cl)C₆H₄ | " | " | " | " | OMe | CH | 134–36 (d)**] |
| 295 | " | " | " | " | " | Me | N | |
| 296 | COCH₂(2-Me)C₆H₄ | " | " | " | " | OMe | CH | |
| 297 | " | " | " | " | " | Me | N | |
| 298 | COCH₂(3-Me)C₆H₄ | " | " | " | " | OMe | CH | 122–24 (d)**] |
| 299 | " | " | " | " | " | Me | N | |
| 300 | COCH₂(4-Me)C₆H₄ | " | " | " | " | OMe | CH | |
| 301 | " | " | " | " | " | Me | N | |
| 302 | COCH₂(2-OMe)C₆H₄ | " | " | " | " | OMe | CH | |
| 303 | " | " | " | " | " | Me | N | |
| 304 | COCH₂(3-OMe)C₆H₄ | " | " | " | " | OMe | CH | |
| 305 | " | " | " | " | " | Me | N | |
| 306 | COCH₂(4-OMe)C₆H₄ | " | " | " | " | OMe | CH | 133–35 (d)**] |
| 307 | " | " | " | " | " | Me | N | |
| 308 | COCH₂(4-CF₃)C₆H₄ | " | " | " | " | OMe | CH | |
| 309 | " | " | " | " | " | Me | N | |
| 310 | COCH₂(2-Br)C₆H₄ | " | " | " | " | OMe | CH | |
| 311 | " | " | " | " | " | Me | N | |
| 312 | COCH₂(2-NO₂)C₆H₄ | H | H | H | OMe | OMe | CH | |
| 313 | " | " | " | " | " | Me | N | |
| 314 | COCH(Me)Ph | " | " | " | " | OMe | CH | 199–201 |
| 315 | " | " | " | " | " | Me | N | |
| 316 | CO-CH₂-(2,4-diCl-C₆H₃) | " | " | " | " | OMe | CH | |
| 317 | " | " | " | " | " | Me | N | |
| 318 | CO-CH₂-(3,4-diOMe-C₆H₃) | " | " | " | " | OMe | CH | 134–36 (d)**] |
| 319 | " | " | " | " | " | Me | N | |
| 320 | CO-CH₂-(2-naphthyl) | " | " | " | " | OMe | CH | |
| 321 | " | " | " | " | " | Me | N | |
| 322 | CO(CH₂)₂Ph | " | " | " | " | OMe | CH | |
| 323 | " | " | " | " | " | Me | N | |
| 324 | COCH₂OPh | " | " | " | " | OMe | CH | |
| 325 | " | " | " | " | " | Me | N | |
| 326 | CO-CH₂-(2-pyridyl) | " | " | " | " | OMe | CH | |
| 327 | " | " | " | " | " | Me | N | |

TABLE 1-continued

Compounds of the formula (Ia)

| Ex. no. | R² | R³ | R⁴ | R⁶ | X | Y | Z | m.p. [°C.] |
|---|---|---|---|---|---|---|---|---|
| 328 | CO-CH₂-(2-thienyl) | " | " | " | " | OMe | CH | 135–37 (d)**] |
| 329 | " | " | " | " | " | Me | N | |
| 330 | CO-CH₂-cyclohexyl | " | " | " | " | OMe | CH | |
| 331 | " | " | " | " | " | Me | N | |
| 332 | " | H | H | Me | OMe | OMe | CH | |
| 333 | " | " | " | " | " | Me | N | |
| 334 | COOMe | " | " | H | " | OMe | CH | 138–41 (d)**] |
| 335 | " | " | " | " | " | Me | CH | |
| 336 | " | " | " | " | " | OMe | N | |
| 337 | " | " | " | " | " | Me | N | |
| 338 | " | " | " | " | " | Cl | CH | |
| 339 | " | " | " | " | Me | Me | CH | |
| 340 | " | " | " | " | OCH₂CF₃ | NMe₂ | N | |
| 341 | " | " | " | " | CF₃ | OMe | N | |
| 342 | " | " | " | " | OCHF₂ | OCHF₂ | CH | |
| 343 | " | " | " | Me | OMe | OMe | CH | |
| 344 | " | " | " | " | " | Me | N | |
| 345 | COOEt | " | " | H | " | OMe | CH | 123–25 (d)**] |
| 346 | " | " | " | " | " | Me | N | |
| 347 | COO(CH₂)₂Cl | " | " | " | " | OMe | CH | 182–83 (d)**] |
| 348 | " | " | " | " | " | Me | N | |
| 349 | COO(CH₂)₂OMe | " | " | " | " | OMe | CH | |
| 350 | " | " | " | " | " | Me | N | |
| 351 | COOPr | " | " | " | " | OMe | CH | |
| 352 | " | " | " | " | " | Me | N | |
| 353 | COO-i-Pr | " | " | " | " | OMe | CH | |
| 354 | " | " | " | " | " | Me | N | |
| 355 | COOCH₂CH=CH₂ | " | " | " | " | OMe | CH | |
| 356 | COOCH₂CH=CH₂ | H | H | H | OMe | Me | N | |
| 357 | COOCH₂C≡CH | " | " | " | " | OMe | CH | |
| 358 | " | " | " | " | " | Me | N | |
| 359 | COOCH₂Ph | " | " | " | " | OMe | CH | |
| 360 | " | " | " | " | " | Me | N | |
| 361 | COOMe | Me | " | " | " | OMe | CH | 143–45 (d)**] |
| 362 | " | " | " | " | " | Me | N | |
| 363 | " | H | Me | " | " | OMe | CH | |
| 364 | " | " | " | " | " | Me | N | |
| 365 | " | Me | " | " | " | OMe | CH | |
| 366 | " | " | " | " | " | Me | N | |
| 367 | COSMe | H | H | " | " | OMe | CH | |
| 368 | " | " | " | " | " | Me | N | |
| 369 | CONHMe | " | " | " | " | OMe | CH | |
| 370 | " | " | " | " | " | Me | N | |
| 371 | CONHEt | " | " | " | " | OMe | CH | 149–52 (d)**] |
| 372 | " | " | " | " | " | Me | N | |
| 373 | CONHPh | " | " | " | " | OMe | CH | 160–63 (d)**] |
| 374 | " | " | " | " | " | Me | N | |
| 375 | CONMe₂ | " | " | " | " | OMe | CH | |
| 376 | " | " | " | " | " | Me | N | |

TABLE 1-continued

Compounds of the formula (Ia)

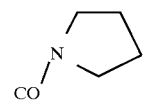

| Ex. no. | R² | R³ | R⁴ | R⁶ | X | Y | Z | m.p. [°C.] |
|---|---|---|---|---|---|---|---|---|
| 377 | CONEt₂ | " | " | " | " | OMe | CH | 157–59 (d)**] |
| 378 | " | " | " | " | " | Me | N | |
| 379 | CSNHEt | " | " | " | " | OMe | CH | |
| 380 | CSNHEt | H | H | H | OMe | Me | N | |
| 381 | CSNHBu | " | " | " | " | OMe | CH | |
| 382 | " | " | " | " | " | Me | N | |
| 383 | 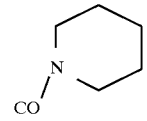 | " | " | " | " | OMe | CH | |
| 384 | " | " | " | " | " | Me | N | |
| 385 | 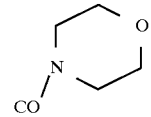 | " | " | " | " | OMe | CH | |
| 386 | " | " | " | " | " | Me | N | |
| 387 | | " | " | " | " | OMe | CH | 129–31 (d)**] |
| 388 | " | " | " | " | " | Me | N | |
| 389 | SO₂Me | " | " | " | " | OMe | CH | |
| 390 | " | " | " | " | " | Me | CH | |
| 391 | " | " | " | " | " | OMe | N | |
| 392 | " | " | " | " | " | Me | N | |
| 393 | " | " | " | " | " | Cl | CH | |
| 394 | " | " | " | " | Me | Me | CH | |
| 395 | " | " | " | " | OCH₂CF₃ | NMe₂ | N | |
| 396 | " | " | " | " | CF₃ | OMe | N | |
| 397 | " | " | " | " | OCHF₂ | OCHF₂ | CH | |
| 398 | " | " | " | Me | OMe | OMe | CH | |
| 399 | " | " | " | " | " | Me | N | |
| 400 | " | Me | " | H | " | OMe | CH | |
| 401 | " | " | " | " | " | Me | N | |
| 402 | " | H | Me | " | " | OMe | CH | |
| 403 | " | " | " | " | " | Me | N | |
| 404 | SO₂Me | Me | Me | H | OMe | OMe | CH | |
| 405 | " | " | " | " | " | Me | N | |
| 406 | SO₂Et | H | H | " | " | OMe | CH | |
| 407 | " | " | " | " | " | Me | N | |
| 408 | SO₂Ph | " | " | " | " | OMe | CH | |
| 409 | " | " | " | " | " | Me | N | |
| 410 | SO₂(4-Me)C₆H₄ | " | " | " | " | OMe | CH | |
| 411 | " | " | " | " | " | Me | N | |
| 412 | SO₂CH₂Cl | " | " | " | " | OMe | CH | |
| 413 | " | " | " | " | " | Me | N | |
| 414 | H | " | COMe | " | " | OMe | CH | |
| 415 | " | " | " | " | " | Me | N | |
| 416 | Me | " | " | " | " | OMe | CH | |
| 417 | " | " | " | " | " | Me | N | |
| 418 | " | Me | " | " | " | OMe | CH | |
| 419 | " | " | " | " | " | Me | N | |
| 420 | H | H | COPh | " | " | OMe | CH | |
| 421 | " | " | " | " | " | Me | N | |

TABLE 1-continued

Compounds of the formula (Ia)

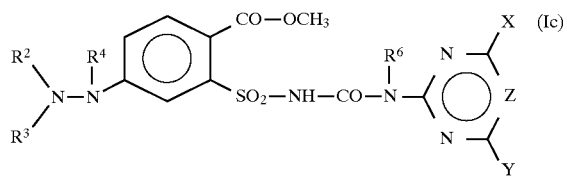

| Ex. no. | R² | R³ | R⁴ | R⁶ | X | Y | Z | m.p. [°C.] |
|---|---|---|---|---|---|---|---|---|
| 422 | " | " | COOMe | " | " | OMe | CH | |
| 423 | " | " | " | " | " | Me | N | |
| 424 | " | " | SO₂Me | " | " | OMe | CH | |
| 425 | " | " | " | " | " | Me | N | |
| 426 | Me | " | " | " | " | OMe | CH | |
| 427 | " | " | " | " | " | Me | N | |
| 428 | " | Me | " | " | " | OMe | CH | |
| 429 | Me | Me | SO₂Me | H | OMe | Me | N | |
| 430 | CHO | Me | H | H | OMe | OMe | CH | |
| 431 | " | " | " | " | " | " | N | |
| 432 | " | " | " | " | " | Cl | CH | |
| 433 | CO-i-Pr | " | " | " | OMe | OMe | CH | 159–61 (d)**] |
| 434 | " | " | " | " | " | " | " | N |

TABLE 2

Compounds of the formula (Ib)

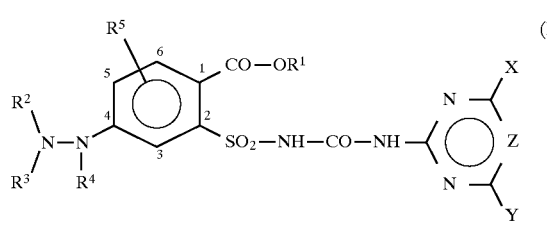

| Ex. No. | R¹ | R² | R³ | R⁴ | R⁵ | X | Y | Z |
|---|---|---|---|---|---|---|---|---|
| 2/1 | Me | CHO | H | H | 3-Me | OMe | OMe | CH |
| 2/2 | " | – | " | " | 6-Me | " | " | " |
| 2/3 | " | " | " | " | 3-Cl | " | " | " |
| 2/4 | " | " | " | " | 5-Cl | " | " | " |
| 2/5 | " | " | " | " | 6-Cl | " | " | " |
| 2/6 | Et | COMe | H | H | H | " | " | " |
| 2/7 | " | " | " | " | " | " | Me | " |
| 2/8 | " | " | " | " | " | " | OMe | N |
| 2/9 | " | " | " | " | " | " | Me | N |
| 2/10 | " | " | " | " | " | " | Cl | CH |
| 2/11 | " | " | " | " | " | Me | Me | CH |
| 2/12 | " | " | " | " | " | OCH₂CF₂ | NMe₂ | N |
| 2/13 | " | " | " | " | " | CF₃ | OMe | N |
| 2/14 | " | " | " | " | " | OCHF₂ | OCHF₂ | CH |
| 2/15 | Pr | " | " | " | " | OMe | OMe | CH |
| 2/16 | " | " | " | " | " | " | Me | N |
| 2/17 | i-Pr | " | " | " | " | " | OMe | H |
| 2/18 | i-Pr | COMe | H | H | H | OMe | Me | N |
| 2/19 | Oxetan-3-yl | " | " | " | " | " | OMe | CH |
| 2/20 | " | " | " | " | " | " | Me | N |
| 2/21 | Et | COCH₂Ph | " | " | " | " | OMe | CH |
| 2/22 | " | " | " | " | " | " | Me | N |

TABLE 3

Compounds of the formula (Ic)

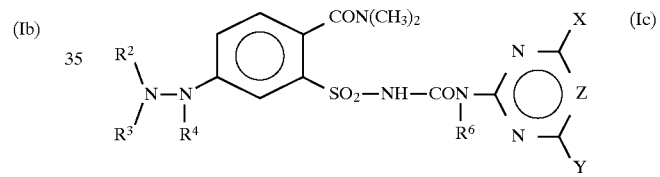

| Ex. No. | R² | R³ | R⁴ | R⁶ | X | Y | Z | m.p. [°C.] |
|---|---|---|---|---|---|---|---|---|
| 3/1 | CHO | H | H | H | OMe | OMe | CH | |
| 3/2 | " | " | " | " | " | Me | N | |
| 3/3 | COMe | " | " | " | " | OMe | CH | 164–66 (Z.) |
| 3/4 | " | " | " | " | " | Me | N | |
| 3/5 | " | " | " | " | " | Cl | CH | |
| 3/6 | " | " | " | " | " | OMe | N | |
| 3/7 | " | " | " | " | " | Me | CH | |
| 3/8 | " | " | " | Me | " | Me | N | |
| 3/9 | COEt | " | " | H | " | OMe | CH | 157–60 (Z) |
| 3/10 | " | " | " | " | " | Me | N | |
| 3/11 | CO-i-Pr | H | H | H | OMe | OMe | CH | 138–42 (d)**] |
| 3/12 | CO-i-Pr | " | " | " | " | Me | N | |
| 3/13 | CO-c-Pr | " | " | " | " | OMe | CH | 148–50 (d)**] |
| 3/14 | " | " | " | " | " | Me | N | |
| 3/15 | CO(CH₂)₃Cl | " | " | " | " | OMe | CH | |
| 3/16 | " | " | " | " | " | Me | N | |
| 3/17 | COPh | " | " | " | " | OMe | CH | |
| 3/18 | " | " | " | " | " | Me | N | |
| 3/19 | COCH₂Ph | " | " | " | " | OMe | CH | |
| 3/20 | " | " | " | " | " | Me | N | |
| 3/21 | COOMe | " | " | " | " | OMe | CH | |
| 3/22 | " | " | " | " | " | Me | N | |
| 3/23 | COO(CH₂)₂Cl | " | " | " | " | OMe | CH | |
| 3/24 | " | " | " | " | " | Me | N | |
| 3/25 | SO₂Me | " | " | " | " | OMe | CH | |
| 3/26 | " | " | " | " | " | Me | N | |
| 3/27 | " | " | Me | " | " | OMe | CH | |
| 3/28 | " | " | " | " | " | Me | N | |

TABLE 4

Compounds of the formula (Id)

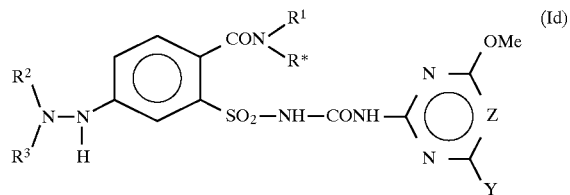

| Ex. no. | R² | R³ | R¹ | R* | Y | Z | m.p. [°C.] |
|---|---|---|---|---|---|---|---|
| 4/1 | COMe | H | $CH_2-CH=CH_2$ | $CH_2-CH=CH_2$ | OMe | CH | |
| 4/2 | " | " | " | " | Me | N | |
| 4/3 | " | " | Et | Et | OMe | CH | |
| 4/4 | " | " | " | " | Me | N | |
| 4/5 | " | " | $CH_2-C\equiv CH$ | $CH_2-C\equiv CH$ | OMe | CH | |
| 4/6 | " | " | " | " | Me | N | |
| 4/7 | CO-c-Pr | " | $CH_2-CH=CH_2$ | Me | OMe | CH | |
| 4/8 | " | " | " | " | Me | N | |
| 4/9 | $COCH_2Ph$ | " | H | Pr | OMe | CH | |
| 4/10 | M | " | " | " | Me | N | |

TABLE 5

Compounds (salts) of the formula (Ie)

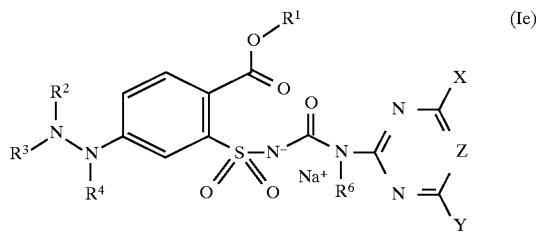

| Ex. no. | R¹ | R² | R³ | R⁴ | R⁶ | X | Y | Z | m.p. [°C.] |
|---|---|---|---|---|---|---|---|---|---|
| 5/1 | Me | CHO | H | H | H | OMe | OMe | CH | |
| 5/2 | " | " | " | " | " | " | Me | N | |
| 5/3 | " | COMe | " | " | " | " | OMe | CH | |
| 5/4 | " | " | " | " | " | " | Me | CH | 218–22 (d)**] |
| 5/5 | " | " | " | " | " | " | OMe | N | 188–91 (d)**] |
| 5/6 | " | " | " | " | " | " | Me | N | |
| 5/7 | " | " | " | " | " | " | Cl | CH | |
| 5/8 | " | " | " | " | " | Me | Me | " | |
| 5/9 | " | " | " | " | " | $OCH_2CF_3$ | $NMe_2$ | N | |
| 5/10 | " | " | " | " | " | $CF_3$ | OMe | " | |
| 5/11 | " | " | " | " | " | $OCHF_2$ | $OCHF_2$ | CH | |
| 5/12 | " | " | " | " | Me | OMe | OMe | " | |
| 5/13 | " | " | " | " | " | " | Me | N | |
| 5/14 | " | COEt | " | " | H | " | OMe | CH | |
| 5/15 | " | " | " | " | " | " | Me | N | |
| 5/16 | " | CO-i-Pr | " | " | " | " | OMe | CH | 200–02 (d)**] |
| 5/17 | " | " | " | " | " | " | Me | N | 216-19 (d)**] |
| 5/18 | " | $COC(CH_3)_3$ | " | " | " | " | OMe | CH | |
| 5/19 | " | " | " | " | " | " | Me | N | |
| 5/20 | " | COPh | " | " | " | " | OMe | CH | |
| 5/21 | Me | $CO(CH_2)_3Cl$ | H | H | H | OMe | Me | N | |
| 5/22 | " | " | " | " | " | " | OMe | CH | |
| 5/23 | " | $COCO_2Me$ | " | " | " | " | Me | N | |
| 5/24 | " | " | " | " | " | " | OMe | CH | |
| 5/25 | " | $COCH_2Ph$ | " | " | " | " | Me | N | |
| 5/26 | " | " | " | " | " | " | OMe | CH | 158–60 (d)**] |
| 5/27 | " | " | " | " | " | " | Me | " | |
| 5/28 | " | " | " | " | " | " | OMe | N | |
| 5/29 | " | " | " | " | " | " | Me | " | |

TABLE 5-continued

Compounds (salts) of the formula (Ie)

| Ex. no. | $R^1$ | $R^2$ | $R^3$ | $R^4$ | $R^6$ | X | Y | Z | m.p. [°C.] |
|---|---|---|---|---|---|---|---|---|---|
| 5/30 | " | " | " | " | " | " | Cl | CH | |
| 5/31 | " | " | " | " | " | Me | Me | " | |
| 5/32 | " | " | " | " | " | $OCH_2CF_3$ | $NMe_2$ | N | |
| 5/33 | " | " | " | " | " | $CF_3$ | OMe | " | |
| 5/34 | " | " | " | " | " | $OCHF_2$ | $OCHF_2$ | CH | |
| 5/35 | " | " | " | " | Me | OMe | OMe | CH | |
| 5/36 | " | " | " | " | " | " | Me | N | |
| 5/37 | " | COOMe | " | " | H | " | OMe | CH | |
| 5/38 | " | " | " | " | " | " | Me | N | |
| 5/39 | " | COOEt | " | " | " | " | OMe | CH | |
| 5/40 | " | " | " | " | " | " | Me | N | |
| 5/41 | " | $COO(CH_2)_2Cl$ | " | " | " | " | OMe | CH | |
| 5/42 | " | " | " | " | " | " | Me | N | |
| 5/43 | " | $SO_2Me$ | " | " | " | " | OMe | CH | |
| 5/44 | " | " | " | " | " | " | Me | N | |

B. FORMULATION EXAMPLES a) A dusting powder is obtained by mixing 10 parts by weight of a compound of the formula (I) and 90 parts by weight of talc, as the inert substance, and comminuting the mixture in an impact mill.

b) A wettable powder which is readily dispersible in water is obtained by mixing 25 parts by weight of a compound of the formula (I), 64 parts by weight of kaolin-containing quartz, as the inert substance, 10 parts by weight of potassium ligninsulfonate and 1 part by weight of sodium oleylmethyltauride, as the wetting and dispersing agent, and grinding the mixture in a pinned disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.) and grinding the mixture to a fineness of less than 5 microns in a ball mill.

d) An emulsifiable concentrate is obtained from 15 parts by weight of a compound of the formula (I), 75 parts by weight of cyclohexanone, as the solvent, and 10 parts by weight of oxyethylated nonylphenol, as the emulsifier.

e) Water-dispersible granules are obtained by mixing 75 parts by weight of a compound of the formula (I), 10 parts by weight of calcium ligninsulfonate, 5 parts by weight of sodium laurylsulfate, 3 parts by weight of polyvinyl alcohol and 7 parts by weight of kaolin, the mixture is ground on a pinned disk mill and the powder is granulated in a fluidized bed by spraying on water as the granulating liquid.

f) Water-dispersible granules are also obtained by homogenizing and precomminuting 25 parts by weight of a compound of the formula (I), 5 parts by weight of sodium 2,2'-dinaphthylmethane 6,6'-disulfonate, 2 parts by weight of sodium oleoylmethyl tauride, 1 part by weight of polyvinyl alcohol, 17 parts by weight of calcium carbonate and 50 parts by weight of water on a colloid mill, subsequently grinding the mixture on a bead mill and atomizing and drying the suspension thus obtained in a spray tower by means of a one-component nozzle.

C. BIOLOGICAL EXAMPLES

1. Action on weeds by the pre-emergence method

Seeds or pieces of rhizome of monocotyledon and dicotyledon weed plants are laid out in sandy loam soil in plastic pots and covered with soil. The compounds according to the invention, formulated in the form of wettable powders or emulsion concentrates, are then applied to the surface of the covering soil as an aqueous suspension or emulsion in various dosages with an amount of water applied, when converted, of 600 to 800 l/ha.

After the treatment, the pots are placed in a greenhouse and are kept under good growth conditions for the weeds. The plant damage or emergence damage is rated visually after emergence of the test plants after a test period of 3 to 4 weeks in comparison with untreated controls. As the test results show, the compounds according to the invention have a good herbicidal pre-emergence activity against a broad spectrum of graminaceous weeds and broadleaved weeds. For example, Examples no. 12, 14, 15, 16, 47, 71, 75, 108, 110, 111, 112, 119, 130, 183, 185, 202, 204, 206, 210, 221, 247, 253, 266, 292, 294, 298, 306, 314, 318, 334, 345, 347, 361, 371, 373, 377, 387, 433, 3/3, 3/9, 3/11, 3/13, 5/4, 5/5, 5/16, 5/17, 5/26 (cf. Tables 1 and 5) have a very good herbicidal action against harmful plants such as Sinapis alba, Chrysanthemum segetum, Avena sativa, Stellaria media, Echinochloa crus-galli, Lolium multiflorum, Setaria spp., Matricaria inodora, Abutilon theophrasti, Amaranthus retroflexus and Panicum miliaceum in the pre-emergence method when applied in an amount of 0.3 kg, preferably 0.1 kg or less of active substance per hectare.

2. Action on weeds by the post-emergence method

Seeds or pieces of rhizome of mono- and dicotyledon weeds are laid out in sandy loam soil in plastic pots, covered with soil and grown in a greenhouse under good growth conditions. Three weeks after sowing, the test plants are treated in the trifoliate stage. The compounds according to the invention, formulated as wettable powders or as emulsion concentrates, are sprayed onto the green parts of the plants in various dosages with an amount of water applied, when converted, of 600 to 800 l/ha. After the test plants have stood in the greenhouse under optimum growth conditions for about 3 to 4 weeks, the action of the preparations is rated visually in comparison with untreated controls. The compositions according to the invention also have a good herbicidal activity against a broad spectrum of economically important graminaceous weeds and broad-leaved weeds in the post-emergence method. For example, Examples no. 12, 14, 15, 16, 47, 71, 75, 108, 110, 111, 112, 119, 130, 183, 185, 202, 204, 206, 210, 221, 247, 253, 266, 292, 294, 298, 306, 314, 318, 334, 345, 347, 361, 371, 373, 377, 387, 433, 3/3, 3/9, 3/11, 3/13, 5/4, 5/5, 5/16, 5/17, 5/26 (cf. Tables 1 and 5) have a very good herbicidal action against harmful plants such as Sinapis alba, Stellaria media, Echinochloa crus-galli, Lolium multiflorum, Chrysanthemum segetum, Setaria spp., Matricaria inodora, Abutilon theophrasti, Amaranthus retroflexus, Panicum miliaceum and Avena sativa in the post-emergence method when applied in an amount of 0.3 kg, preferably 0.1 kg or less of active substance per hectare.

3. Crop plant tolerance

In further experiments in the greenhouse, seeds of a relatively large number of crop plants and weeds are laid out in sandy loam soil and covered with soil. Some of the pots are treated immediately as described under Section 1, and the others are placed in a greenhouse until the plants have developed two to three true leaves, and are then sprayed with the substances of the formula (I) according to the invention in various dosages as described under Section 2. Four to five weeks after the application and standing time in the greenhouse, it is found by visual rating that the compounds according to the invention leave dicotyledonous crops such as, for example, soya, cotton, rape, sugar beet and potatoes, undamaged by the pre- and post-emergence methods even at high dosages of active compound. Some substances furthermore also protect graminaceous crops, such as, for example, barley, wheat, rye, sorghum, millet, maize or rice. Some of the compounds of the formula (I) have a high selectivity and are therefore suitable for controlling undesirable plant growth in agricultural crops.

We claim:

1. A compound of the formula (I) or a salt thereof

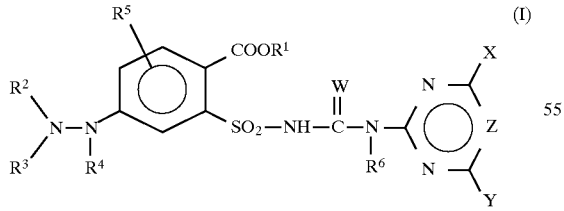

in which $R^1$ is H, $(C_1-C_6)$alkyl, $(C_3-C_6)$alkenyl or $(C_3-C_6)$alkynyl, where each of the last three radicals mentioned is unsubstituted or substituted by one or more radicals from the group consisting of halogen, phenyl, $(C_1-C_4)$alkoxy, $(C_1-C_4)$alkylthio and $[(C_1-C_4)$alkoxy]-carbonyl, or $(C_3-C_6)$cycloalkyl, $(C_3-C_6)$cycloalkyl $(C_1-C_3)$alkyl, heterocyclyl having 3 to 6 ring atoms or heterocyclyl-$(C_1-C_3)$alkyl having 3 to 6 ring atoms, where each of the last 4 radicals mentioned is unsubstituted or substituted by one or more radicals selected from the group consisting of halogen, $(C_1-C_4)$alkyl and $(C_1-C_4)$alkoxy, $R^2$, $R^3$ and $R^4$ independently of one another are a radical of the formula $A^1$ or $A^2$, where at least one of the radicals $R^2$, $R^3$ and $R^4$ has the meaning of $A^1$, $R^5$ is H, halogen, $NO_2$, CN, $(C_1-C_4)$alkyl, $(C_1-C_4)$alkoxy, $[(C_1-C_4)]$carbonyl or $[(C_1-C_4)$alkoxy]carbonyl, where each of the last four radicals mentioned is unsubstituted or substituted in the alkyl part by one or more halogen atoms, $R^6$ is H or $(C_1-C_4)$alkyl, $A^1$ is a substituted aliphatic hydrocarbon radical having 1 to 6 carbon atoms in the hydrocarbon part and one or more substituents, where the substituents are selected from the group consisting of halogen, $(C_1-C_4)$alkoxy, $(C_1-C_4)$alkylthio, $(C_1-C_4)$alkylsulfonyl, $[(C_1-C_4)$alkyl]carbonyl, $[(C_1-C_4)$alkoxy]-carbonyl, CN, substituted or unsubstituted phenyl and $(C_3-C_6)$cycloalkyl, or $(C_2-C_6)$alkenyl or $(C_2-C_6)$alkynyl, or an acyl radical of the formula

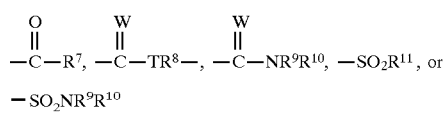

$R^7$ is H, $(C_1-C_8)$alkyl, $(C_2-C_6)$alkenyl or $(C_2-C_6)$alkynyl, where each of the last three radicals mentioned is unsubstituted or substituted by one or more radicals selected from the group consisting of halogen, $(C_1-C_4)$alkoxy, $(C_1-C_4)$alkylthio, phenoxy, $[(C_1-C_4)$alkoxy]carbonyl, unsubstituted or substituted heterocyclyl and unsubstituted or substituted phenyl, or unsubstituted or substituted $(C_3-C_6)$cycloalkyl, unsubstituted or substituted phenyl, unsubstituted or substituted heterocyclyl or $[(C_1-C_4)$alkoxy]carbonyl, $R^8$ is the radical of the formula $R^7$, apart from hydrogen, $R^9$ and $R^{10}$ independently of one another are H, $(C_1-C_6)$alkyl, $(C_3-C_6)$alkenyl or $(C_3-C_6)$alkynyl, where each of the last three radicals mentioned is unsubstituted or substituted by one or more radicals selected from the group consisting of halogen, $(C_1-C_4)$alkoxy, $(C_1-C_4)$alkylthio and $[(C_1-C_4)$alkyl]carbonyl, or unsubstituted or substituted phenyl, or $R^9$ and $R^{10}$, together with the N atom, are an aliphatic heterocyclic ring having 5 or 6 ring members, which can optionally contain a further hetero atom selected from the group consisting of N and O and is unsubstituted or mono- or poly-substituted by $(C_1-C_4)$alkyl or an oxo group, $R^{11}$ is $(C_1-C_6)$alkyl, $(C_3-C6)$alkenyl or $(C_3-C_6)$alkynyl, where each of the last three radicals mentioned is unsubstituted or substituted by one or more radicals from the group consisting of halogen, $(C_1-C_4)$alkoxy, $(C_1-C_4)$alkylthio and phenyl, or phenyl, which is unsubstituted or substituted by one or more radicals selected from the group consisting of halogen, CN, $NO_2$ $(C_1-C_4)$alkyl, $(C_1-C_4)$haloalkyl and $(C_1-C_4)$alkoxy, $A^2$ is a group recited for $A^1$ or is hydrogen or $(C_1-C_6)$alkyl, Q is O or NR*, R* is H, $(C_1-C_4)$alkyl, $(C_3-C_4)$alkenyl or $(C_3-C_4)$ alkynyl, where each of the last three radicals mentioned is unsubstituted or substituted by one or more radicals selected from the group consisting of halogen, $(C_1-C_4)$ alkoxy and $(C_1-C_4)$alkylthio, W is an oxygen or sulfur atom, and X and Y independently of one another are H, halogen, $(C_1-C_4)$alkyl, $(C_1-C_4)$alkoxy or $(C_1-C_4)$alkylthio, where each of the last three radicals mentioned is unsubstituted or substituted by one or more radicals selected from the group consisting of halogen, $(C_1-C_4)$ alkoxy and $(C_1-C_4)$alkylthio, or mono- or di-[$(C_1-C_4)$ alkyl]amino, $(C_3-C_6)$cycloalkyl, $(C_2-C_5)$alkenyl, $(C_2-C_5)$alkynyl, $(C_2-C_5)$alkenyloxy or $(C_2-C_5)$ alkynyloxy, wherein heterocyclyl means a heterocyclic radical selected from the group consisting of pyridyl, pyrimidinyl, pyridazinyl, pyrazinyl, thienyl, thiazolyl, oxazolyl, furyl, pyrrolyl, pyrazolyl, imidazolyl, piperidyl, piperazinyl, dioxolanyl, morpholinyl and an aliphatic heterocyclyl radical having 3 to 6 ring atoms and containing 1 hetero atom selected from the group consisting of N, O, S, SO and $SO_2$, and wherein substituted, if not further specified, means substituted with one or more substitutents selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, acylamino, mono-, dialkylamino, alkylsulfinyl, aloalkylsulfinyl, alkylsulfonyl, haloalkylsulfonyl and, in the case of cyclic radicals, alkyl, haloalkyl, alkenyl, alkynyl, alkenyloxy and alkynyloxy wherein radicals with carbon atoms have 1 to 4 carbon atoms.

2. A compound or salt thereof as claimed in claim 1, in which $A^1$ is $(C_1-C_6)$alkyl, which is substituted by one or more radicals selected from the group consisting of halogen, $(C_1-C_4)$alkoxy, $(C_1-C_4)$alkylthio, $(C_1-C_4)$ alkylsulfonyl, [$(C_1-C_4)$alkoxy]carbonyl, CN, phenyl and $(C_1-C_6)$cycloalkyl, or $(C_3-C_6)$alkenyl or $(C_3-C_6)$ alkynyl, where each of the last two radicals mentioned is unsubstituted or substituted by one or more halogen atoms, or a group of the formula

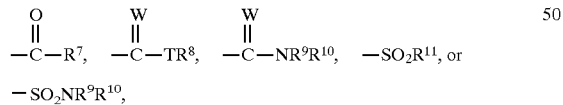

$A^2$ is a group recited for $A^1$ or is hydrogen or $(C_1-C_4)$ alkyl, and wherein heterocyclyl means a heterocyclic radical selected from the group consisting of piperidyl, piperazinyl, dioxolanyl, morpholinyl and an aliphatic heterocyclic radical having 3 to 6 ring atoms and containing 1 hetero atom selected from the group consisting of N, O, S, SO and $SO_2$ and wherein substituted, if not further specified, means substituted with 1, 2 or 3 substituents selected from the group consisting of halogen, $(C_1-C_4)$alkyl, $(C_1-C_4)$haloalkyl, $(C_1-C_4)$alkoxy, $(C_1-C_4)$haloalkoxy, nitro and cyano.

3. A compound or a salt thereof as claimed in claim 1, in which $R^1$ is $(C_1-C_6)$alkyl, which is unsubstituted or substituted by one or more radicals selected from the group consisting of halogen and $(C_1-C_4)$alkoxy, or $(C_3-C_4)$ alkenyl or $(C_3-C_4)$alkynyl, or heterocyclyl, $R^2$ is a group of the formula

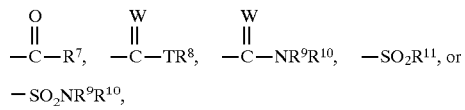

$R^3$ is H, $(C_1-C_4)$alkyl, which is unsubstituted or substituted by one or more radicals selected from the group consisting of halogen, $(C_1-C_4)$alkoxy, $(C_1-C_4)$-alkylthio, [$(C_1-C_4)$alkoxy]carbonyl and phenyl, or $(C_3-C_4)$alkenyl or $(C_3-C_4)$alkynyl, or $R^4$ is H, $(C_1-C_4)$alkyl, which is unsubstituted or substituted by one or more radicals selected from the group consisting of halogen, $(C_1-C_4)$alkoxy, $(C_1-C_4)$ alkylthio, [$(C_1-C_4)$alkoxy]carbonyl and phenyl, or $(C_3-C_4)$alkenyl or $(C_3-C_4)$alkynyl, $R^5$ is H, $(C_1-C_4)$alkyl, $(C_1-C_4)$haloalkyl, $(C_1-C_4)$alkoxy or halogen, $R^6$ is H or methyl, $R^7$ is H, $(C_1-C_6)$alkyl, which is unsubstituted or substituted by one or more radicals selected from the group consisting of halogen, $(C_1-C_4)$alkoxy, $(C_1-C_4)$ alkylthio, [$(C_1-C_4)$alkoxy]carbonyl and unsubstituted or substituted phenyl, or $(C_2-C_4)$alkenyl, $(C_2-C_4)$ alkynyl, $(C_3-C_6)$cycloalkyl, [$(C_1-C_4)$alkoxy]carbonyl, unsubstituted or substituted phenyl or unsubstituted or substituted heterocyclyl, $R^8$ is $(C_1-C_4)$alkyl, $(C_1-C_4)$haloalkyl, $(C_3-C_4)$alkenyl, $(C_3-C_4)$alkynyl or $(C_3-C_6)$cycloalkyl, $R^9$ and $R^{10}$ independently of one another are H, $(C_1-C_4)$ alkyl, which is unsubstituted or substituted by one or more radicals from the group consisting of halogen and $(C_1-C_4)$alkoxy, or $(C_3-C_4)$alkenyl or $(C_3-C_4)$alkynyl, or $R^9$ and $R^{10}$, together with the N atom, are a heterocyclic ring having 5 or 6 members, which can optionally contain a further hetero atom selected from the group consisting of N and O and is unsubstituted or mono- or polysubstituted by $(C_1-C_4)$alkyl or an oxo group, $R^{11}$ is $(C_1-C_6)$alkyl, $(C_1-C_4)$haloalkyl or phenyl, which is unsubstituted or substituted by one or more radicals selected from the group consisting of halogen, $(C_1-C_4)$ alkyl and $(C_1-C_4)$alkoxy, R* is H or $(C_1-C_4)$alkyl, X and Y independently of one another are $(C_1-C_4)$alkyl or $(C_1-C_4)$alkoxy, where the last two radicals mentioned are unsubstituted or substituted by one or more halogen atoms, or $(C_1-C_4)$alkylthio, halogen or mono- or di[ $(C_1-C_2)$alkyl]amino and/or W is an oxygen atom, and wherein heterocyclyl means a heterocyclic radical selected from the group consisting of piperidyl, piperazinyl, dioxolanyl, morpholinyl and an aliphatic heterocyclic radical having 3 to 8 ring atoms and containing 1 hetero atom selected from the group consisting of N, O, S, SO and $SO_2$, and wherein substituted, if not further specified, means substituted with 1, 2 or 3 substituents from the group consisting of halogen, $(C_1–C_4)$alkyl, $(C_1–C_4)$haloalkyl, $(C_1–C_4)$alkoxy, $(C_1–C_4)$haloalkoxy, nitro and cyano.

4. A herbicidal or plant growth-regulating composition which comprises one or more of a compound of formula (I) according to claim 1 or a salt thereof and an inert formulating auxiliary.

5. A method of controlling harmful plants or of regulating the growth of plants which comprises applying an effective amount of one or more of a compound of formula I according to claim 1 or a salt thereof to the harmful plant or plants, plant seeds thereof or an area which they grow.

* * * * *